(12) United States Patent
Singh et al.

(10) Patent No.: US 12,370,203 B2
(45) Date of Patent: Jul. 29, 2025

(54) PHARMACEUTICAL COMPOSITIONS AND METHODS OF MAKING ON DEMAND SOLID DOSAGE FORMULATIONS

(71) Applicant: Eastern Virginia Medical School, Norfolk, VA (US)

(72) Inventors: Onkar N. Singh, Fairfax, VA (US); Timothy J. McCormick, Wilmington, DE (US); Vivek Agrahari, Leesburg, VA (US); Melissa Peet, McLean, VA (US); Meredith Roberts Clark, Bethesda, MD (US); Jill Schwartz, Garrett Park, MD (US); Gustavo F. Doncel, McLean, VA (US)

(73) Assignee: Eastern Virginia Medical School, Norfolk, VA (US)

( * ) Notice: Subject to any disclaimer, the term of this patent is extended or adjusted under 35 U.S.C. 154(b) by 854 days.

(21) Appl. No.: 17/287,030

(22) PCT Filed: Oct. 23, 2019

(86) PCT No.: PCT/US2019/057645
§ 371 (c)(1),
(2) Date: Apr. 20, 2021

(87) PCT Pub. No.: WO2020/086705
PCT Pub. Date: Apr. 30, 2020

(65) Prior Publication Data
US 2021/0379089 A1 Dec. 9, 2021

Related U.S. Application Data

(60) Provisional application No. 62/749,539, filed on Oct. 23, 2018.

(51) Int. Cl.
| | | |
|---|---|---|
| A61K 31/675 | (2006.01) | |
| A61K 9/00 | (2006.01) | |
| A61K 31/4164 | (2006.01) | |
| A61K 31/47 | (2006.01) | |
| A61K 31/65 | (2006.01) | |
| A61K 31/7052 | (2006.01) | |
| A61K 31/7056 | (2006.01) | |
| A61P 31/18 | (2006.01) | |

(52) U.S. Cl.
CPC .......... *A61K 31/675* (2013.01); *A61K 9/0031* (2013.01); *A61K 9/0034* (2013.01); *A61K 31/4164* (2013.01); *A61K 31/47* (2013.01); *A61K 31/65* (2013.01); *A61K 31/7052* (2013.01); *A61K 31/7056* (2013.01); *A61P 31/18* (2018.01)

(58) Field of Classification Search
CPC ................ A61K 31/675; A61K 9/0031; A61K 9/0034; A61K 31/4164; A61K 31/47; A61K 31/65; A61K 31/7052; A61K 31/7056; A61P 31/18
See application file for complete search history.

(56) References Cited

U.S. PATENT DOCUMENTS

| | | | | |
|---|---|---|---|---|
| 6,328,991 | B1 * | 12/2001 | Myhling | ............... A61F 6/08 514/843 |
| 2005/0009811 | A1 * | 1/2005 | Albano | ............... A61K 9/2054 514/220 |
| 2011/0159091 | A1 | 6/2011 | Stone et al. | |
| 2012/0219602 | A1 | 8/2012 | Flack et al. | |
| 2013/0217644 | A1 * | 8/2013 | Mayes | ............... A61P 31/14 514/47 |
| 2014/0134246 | A1 | 5/2014 | Venkatesh et al. | |
| 2016/0000797 | A1 * | 1/2016 | Checcone | ............ A61K 31/565 424/432 |

FOREIGN PATENT DOCUMENTS

| | | |
|---|---|---|
| WO | WO-2006/017044 A2 | 2/2006 |
| WO | WO-2007/092326 A2 | 8/2007 |
| WO | WO-2012151237 A1 | 11/2012 |
| WO | WO-2018/069888 A1 | 4/2018 |
| WO | WO-2018/183285 A1 | 10/2018 |

OTHER PUBLICATIONS

"Povidone K30", Drugs.com, https://www.drugs.com/inactive/povidone-k30-373.html, Jul. 2018 (2 pages).
Friend, D.R., et al., "Assessment of topical microbicides to prevent HIV-1 transmission: concepts, testing, lessons learned," Antiviral research, 99, pp. 391-400, Jul. 2013 (10 pages).
Garg, S., et al., Advances in development, scale-up and manufacturing of microbicide gels, films, and tablets, Antiviral research, 88 Suppl 1, S19-29, 2010 (11 pages).
International Search Report and Written Opinion, mailed Jan. 17, 2020, for PCT International Application No. PCT/US2019/057645 (14 pages).
Jhunjhunwala, Kunal S., "Design and Evaluation of a Topical Rectal Specific Microbicide for HIV prevention," Submitted to Graduate Faculty of School of Pharmacy, University of Pittsburgh, 2015 (64 pages).
Joglekar, N. S., et al., Acceptability of Praneem polyherbal vaginal tablet among HIV uninfected women & their male partners in Pune, India —Phase I study, The Indian journal of medical research, 123, pp. 547-552, 2006 (6 pages).

(Continued)

*Primary Examiner* — Joseph K McKane
*Assistant Examiner* — Quincy McKoy
(74) *Attorney, Agent, or Firm* — Meunier Carlin & Curfman LLC

(57) ABSTRACT

A pharmaceutical composition and methods for using the pharmaceutical composition are disclosed. The pharmaceutical composition may include a therapeutically effective amount of one or more antiviral active pharmaceutical ingredients and a pharmaceutically acceptable excipient. The pharmaceutical composition may be a solid dosage form, wherein the solid dosage form provides sustained release of the antiviral active pharmaceutical ingredient when administered as a vaginal or rectal insert.

25 Claims, 20 Drawing Sheets

(56) References Cited

OTHER PUBLICATIONS

Li, B. et al., Shape of vaginal suppositories affects willingness-to-try and preference, Antiviral research, 97, pp. 280-284, 2013 (5 pages).
Li, B. et al., User preferences in a carrageenan-based vaginal drug delivery system, Plos One, vol. 8, Issue 1, e54975, 2013 (9 pages).
Mandal, Subhra, et al., "Tenofovir alafenamide and elvitegravir loaded nanoparticles for long-acting prevention of HIV-1 vaginal transmission," AIDS. Feb. 20, 2017, 31(4): 469-476, doi:10.1097/QAD.0000000000001349 (Author Manuscript—available in PMC Feb. 20, 2018—(15 pages).
Mauck, Christine, et al., Pharmacokinetics of Tenofovir and Emtricitabine Delivered by Vaginal Tablets, IAS 2015, $8^{th}$ IAS conference on HIV Pathogenesis, Treatment and Prevention, held Jul. 19-22, 2015 in Vancouver, Canada (2 pages).
Nel, A. M., Acceptability of vaginal film, soft-gel capsule, and tablet as potential microbicide delivery methods among African women, Journal of women's health, vol. 20, No. 8, pp. 1207-1214, 2011 (11 pages).
Nelson, A. G., et al., Drug delivery strategies and systems for HIV/AIDS pre-exposure prophylaxis and treatment, Journal of controlled release, 219, pp. 669-680, 2015 (12 pages).
Office Action issued for Mexican Application No. MX/a/2021/004553, dated Mar. 19, 2024.
Office Action issued for Australian Application No. 2019365204, dated Jul. 11, 2024.
Clercq, E. D., "Role of tenofovir alafenamide (TAF) in the treatment and prophylaxis of HIV and HBV infections," Biochemical Pharmacology, vol. 153, pp. 2-11 (available online Dec. 7, 2017).
Communication pursuant to Article 94(3) EPC issued in 19877183.4, mailed Feb. 12, 2025.
English translation of Office Action issued in MX/a/2021/004553, mailed Sep. 19, 2024.
Office Action issued in Mexican Application No. MX/a/2021/004553, mailed Feb. 26, 2025.

\* cited by examiner

PHARMACEUTICAL COMPOSITIONS AND METHODS OF MAKING ON DEMAND SOLID DOSAGE FORMULATIONS

CROSS-REFERENCE TO RELATED APPLICATION

This application is a U.S. National Stage application under 35 U.S.C. § 371 of International Patent Application No. PCT/US2019/057645, filed on Oct. 23, 2019, which claims the benefit of priority from U.S. Provisional Application No. 62/749,539, filed on Oct. 23, 2018, the contents of each of these applications are incorporated by reference herein in its entirety.

STATEMENT CONCERNING GOVERNMENT RIGHTS IN FEDERALLY-SPONSORED RESEARCH

This invention was made with government support under contract AID-OAA-A-14-00010 (MAPS2) awarded by United States Agency for International Development (USAID). The government has certain rights in the invention.

BACKGROUND OF THE INVENTION

Daily Truvada (FTC/TDF) oral tablet is the only approved product as of 2012 for HIV prophylaxis. The daily Truvada tablet regimen has adherence issues with high pill burden. Another product for HIV prophylaxis is once a month use of dapivirine ring in women by IPM. Currently, IPM is pursuing approvals from global and national regulatory authorities for the ring's use in countries where women face the highest risk for HIV. A third HIV prevention product in Phase III development stage is long acting (LA) cabotegravir (CAB) injectable by ViiV. CAB LA Injectable is irreversible, needs oral lead-in, and raises concerns for resistance due to potential issue of the long PK tail.

Therefore, there is a need for an on demand topical pre-exposure prophylaxis (PrEP) product or post-exposure product, which will provide more desirable options to women and men, such as vaginal and rectal on demand topical PrEP. On-demand topical PrEP for HIV prevention has several advantages over a daily oral PrEP regimen including reduced costs, limited drug toxicity, decreased risk of resistance, and potential to increase adherence.

SUMMARY OF THE INVENTION

This application discloses pharmaceutical compositions and methods of making solid dosage forms containing antiviral active pharmaceutical ingredients in the form of an insert. More particularly, the present application discloses solid dosage forms comprising tenofovir alafenamide fumarate (TAF) and elvitegravir (EVG) in the form of an insert. The insert formulation disclosed herein is suitable for delivery of an antiviral drug or combination of antiviral drugs for on demand treatment and/or prevention of HIV, HBV and HSV infection pre and post sexual activity. This formulation composition also overcomes the chemical stability issues associated with the TAF. In addition, antiviral drugs used in an insert form to deliver drugs at the vaginal and/or rectal targeted local sites and to the general circulation is beneficial and herewith discloses a promising pre-clinical in vitro data for the prevention of HIV and HSV. The insert may be a solid dosage form like a tablet with directions for ease of administration. The insert described herein may provide several advantages over other dosage forms for prophylaxis of HIV, HSV and HBV, such as on demand topical delivery of drugs, targeted delivery to the site (e.g., vaginal mucosa or rectal mucosa), improved adherence due to increased effectiveness, discrete (small), easy to use, simple, easy to carry anywhere and any place, and self-administered. Inserts are economical with relatively low manufacturing cost, safe and acceptable, provide more forgiveness with more flexible dosing options, such as before or after sexual activity.

In one aspect, disclosed herein is a pharmaceutical composition comprising a therapeutically effective amount of one or more antiviral active pharmaceutical ingredients and one or more pharmaceutically acceptable excipients, wherein the pharmaceutical composition provides a therapeutically effective amount of the antiviral active pharmaceutical ingredient to vaginal or rectal mucosa when administered topically. In accordance with certain aspects, the pharmaceutical composition may be a solid dosage form, wherein the solid dosage form provides sustained release of the antiviral active pharmaceutical ingredient when administered as a vaginal or rectal insert.

In another aspect, disclosed herein is a solid dosage form comprising a therapeutically effective amount one or more antiviral active pharmaceutical ingredients and a one or more pharmaceutically acceptable excipient, wherein the solid dosage form exhibits a mucoadhesive detachment force of at least 0.1 N when measured in accordance with test method described herein with porcine vaginal mucosa.

In some embodiments, the dosage form comprises about 1.5% to about 15% by weight of antiviral active pharmaceutical ingredients.

In some embodiments, the one or more active pharmaceutical ingredients comprise an NRTI and an integrase inhibitor.

In some embodiments, the one or more active pharmaceutical ingredients comprise tenofovir alafenamide fumarate (TAF) and elvitegravir (EVG). In some embodiments, the tenofovir alafenamide fumarate (TAF) is present in an amount from about 2% to 8% TAF as free base and said elvitegravir (EVG) is present in an amount from about 1.6% to 4.8%.

In some embodiments, the one or more pharmaceutically acceptable excipient comprises povidone. In some embodiments, the povidone comprises povidone K29/32, povidone K30 or a mixture thereof.

In some embodiments, the one or more pharmaceutically acceptable excipient comprises a water soluble disintegrant, such as poloxamer 188, which may be present in an amount from 0.5 to 4% by weight.

In some embodiments, the one or more pharmaceutically acceptable excipient comprises a filler, such as lactose, which may be present in an amount from about 25% to 75% by weight.

In some embodiments, the one or more pharmaceutically acceptable excipient comprises a diluent such as a sugar alcohol, which may be present in an amount from about 5% to 30% by weight. In some embodiments, the sugar alcohol is selected from the group consisting of mannitol, glycerol, erythritol, xylitol, sorbitol, isomalt, maltitol, lactitol, and mixtures thereof.

In some embodiments, the one or more pharmaceutically acceptable excipient comprises a bioadhesive polymer, such as PEG, more particularly PEG 6000 or PEG 8000, which may be present in an amount from about 5 to 30% by weight.

In some embodiments, the one or more pharmaceutically acceptable excipient comprises a lubricant, which may be selected from the group consisting of magnesium stearate, stearic acid, sodium stearyl fumarate, glycerol monostearate, colloidal silicon dioxide, talc, calcium stearate and mixtures thereof. The lubricant may be present in a concentration ranging from 0.2-4% by weight, preferably 0.5% to 3% by weight and most preferably 1.0 to 2.0% by weight.

In some embodiments, the one or more pharmaceutically acceptable excipient comprises a hydrophilic excipient selected from the group consisting of hyaluronic acid, maltodextrin, dextrin, cyclodextrin, Vitamin E TPGS, Pluronics, amino acids, gelatins, polyethylene glycols, poly (ethylene oxide) (PEO), poly(vinylpyrrolidinone) (PVP), cellulose ethers and mixtures thereof.

In some embodiments, the dosage form comprises from about 1.5% to about 15% by weight of one or more antiviral active pharmaceutical ingredients, a binder in an amount from about 0.5% to about 8% by weight, a water-soluble disintegrating agent in an amount from about 0.5% to about 4% by weight and a bioadhesive polymer in an amount from about 5% to about 30% by weight. In some embodiments, the one or more antiviral active pharmaceutical ingredients comprises TAF and EVG, the binder comprises povidone, the water soluble disintegrating agent comprises poloxamer 188 and the bioadhesive polymer comprises PEG 8000.

In some embodiments, the dosage form further comprises an antibiotic. In some embodiments, the antibiotic may be selected from the group consisting of tetracyclines, macrolides, lincosamides, nitroimidazoles and mixtures thereof. In some embodiments, the antibiotic may be selected from the group consisting of doxycycline, doxycycline hyclate, doxycycline anhydrous, doxycycline monohydrate, azithromycin, clindamycin, metronidazole, tinadazole, secnidazole and mixtures thereof.

In some embodiments, a method for treating or preventing a viral infection in a subject comprising administering a solid dosage form disclosed herein to the subject. The dosage form can be administered pre or post sexual activity. In accordance with certain aspects, a method for further treating another infection, such as bacterial infection, is also described.

In some embodiments, the viral infection being treated or prevented may be selected from the group consisting of HIV, HSV and HBV. In some embodiments, the bacterial infection being treated may be selected from the group consisting of *chlamydia*, gonorrhea, bacterial vaginosis, trichomoniasis and syphilis. In some embodiments, the viral infection being treated or prevented is HIV, HSV or HBV and the bacterial infection being treated is *chlamydia*, gonorrhea or syphilis.

BRIEF DESCRIPTION OF DRAWINGS

FIG. 1A shows results for co-exposure; FIG. 1B shows results for 7 hour pre-exposure; and FIG. 1C shows results for 9 hour post-exposure.

DETAILED DESCRIPTION OF THE INVENTION

Figure 1A:
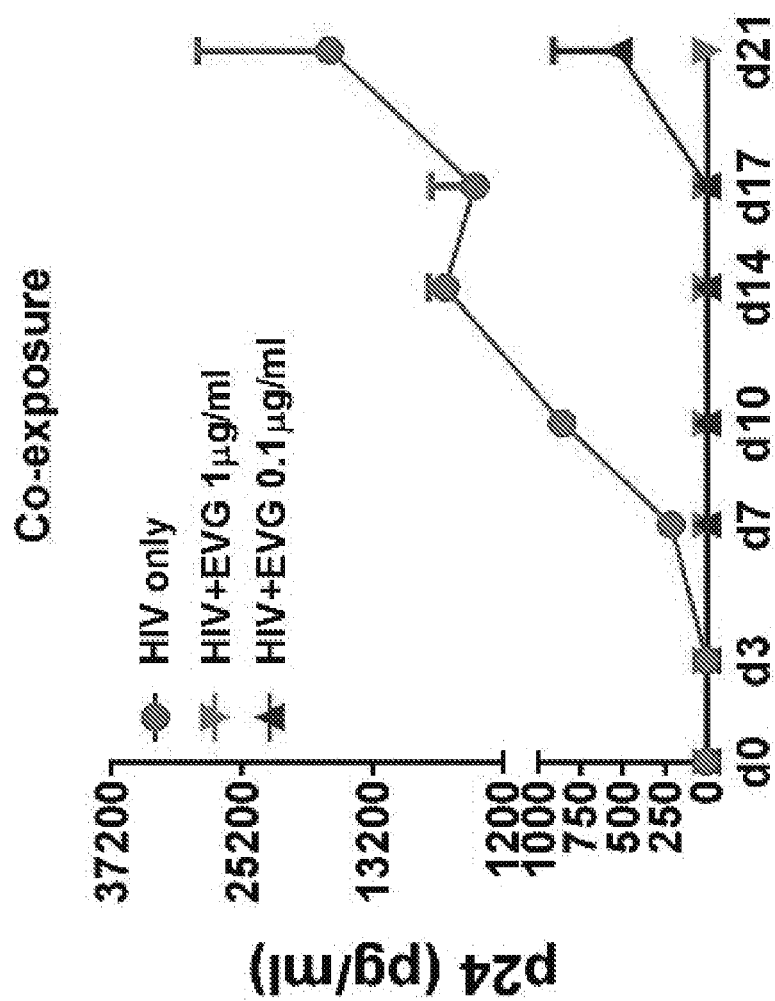
FIGS. 1A, 1B and 1C show EVG dose response plots on p24 production. Representation of p24 antigen expression from three different donors is shown under three different conditions.

The terms "treatment," "treating," "treat," "therapy," "therapeutic," and the like are used herein to refer generally to obtaining a desired pharmacological and/or physiological effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a subject, and includes: (a) preventing the disease or symptom from occurring in a subject which may be predisposed to the disease or symptom, may or may not be diagnosed as having it; (b) inhibiting the disease symptom, i.e., arresting its development; or (c) relieving the disease symptom, i.e., causing regression of the disease or symptom.

The term "pharmaceutically acceptable carrier," as used herein, refers to any and all solvents, dispersion media, coatings, antibacterial and antifungal agent, isotonic and absorption delaying agents for pharmaceutical active substances as are well known in the art.

The term "active pharmaceutical ingredient", "pharmaceutical" or "agent", as used herein, includes a pharmaceutically acceptable and therapeutically effective compound, pharmaceutically acceptable salts, stereoisomers and mixtures of stereoisomers, solvates (including hydrates), polymorphs, or prodrugs thereof. Unless otherwise indicated, when referring to a drug in the descriptions of the various embodiments of the invention, the reference encompasses the base drug, pharmaceutically acceptable salts, stereoisomers and mixtures of stereoisomers, solvates (including hydrates), polymorphs, or prodrugs thereof. Except insofar as any conventional media or agent is incompatible with the agent, its use in the therapeutic pharmaceutical compositions is contemplated. Supplementary compounds or biological pharmaceuticals can also be incorporated into the pharmaceutical compositions.

As used herein, the term "excipient" refers to the additives used to convert a pharmaceutical agent into a form suitable for its intended purpose. For pharmaceutical compositions of the present invention suitable for administration to a human, the term "excipient" includes those excipients described in the HANDBOOK OF PHARMACEUTICAL EXCIPIENTS, American Pharmaceutical Association, 2nd Ed. (1994), which is herein incorporated in its entirety. The term "excipients" is meant to include fillers, binders, disintegrating agents, lubricants, solvents, suspending agents, dyes, extenders, surfactants, auxiliaries and the like.

The expression "therapeutically effective amount" refers to an amount of an agent disclosed herein, that is effective for preventing, ameliorating, treating or delaying the onset of a disease or condition.

The pharmaceutical compositions of the inventions can be administered to any animal that can experience the beneficial effects of the agents of the invention. Such animals include humans and non-humans such as primates, pets and farm animals.

The term "bioadhesive material" refers to a material that improves adherence of the pharmaceutical composition to mucosa or similar biological surface compared to the adherence of the pharmaceutical composition without the bioadhesive material. Non-limiting examples of bioadhesive materials include bioadhesive polymers such as povidone and hydroxypropylcellulose.

The term "sustained-release" refers to a dosage form in which the rate of release of the active is spread over a period of time (for example, 15 minutes, 30 minutes 45 minutes, 60 minutes, 90 minutes, 120 minutes) as opposed to immediate (less than one minute) release of the active.

The present application provides on demand solid dosage forms for administration of antiviral drugs vaginally or rectally. The vaginal and rectal routes of administration provide unique anatomical and physiological advantages such as: (a) Potential to increase the local or systemic absorption of the drug substances due to large surface area and rich blood supply and (b) Vaginal or rectal route of drug delivery avoids the hepatic and intestinal first-pass metabolism. Accordingly, antiviral drug administered via the vaginal or rectal route may provide for enhanced bioavailability and reduction in the dosing level over other routes such as oral dosage forms. Hence, the present application provides a cost effective, affordable, portable, ease of use technology for prevention and/or treatment of various viral diseases such as HIV through administration of various antiviral drugs. In accordance with certain embodiments, the disclosed dosage forms comprise (a) NRTI: Tenofovir Alafenamide Fumarate (TAF) salt form and (b) Integrase Inhibitor: Elvitegravir (EVG) in the form of an on demand insert for prevention of HIV. Currently, there is no such product available. Importantly, from drug delivery perspective, topical inserts are versatile, economical, stable, and well-suited for event-driven, on-demand delivery of antiretroviral (ARV) drugs and other small molecules.

The present application, in accordance with certain embodiments, provides dosage forms that exhibit sufficient mucoadhesive properties to adhere to the vaginal or rectal mucosa and provide release of the active pharmaceutical ingredients. Although the present application describes in detail sustained release compositions, other release profiles such as immediate release, pulsed release and extended release may also be useful in accordance with particular embodiments. The mucoadhesive sustained-release vaginal or rectal dosage form may comprise a combination of antiviral active pharmaceutical ingredients. In accordance with certain embodiments, the solid dosage form may exhibit a mucoadhesive detachment force of at least 0.1 N, more particularly at least 0.2 N, 0.25 N or in some cases, 0.3 N when measured in accordance with test method described herein with porcine vaginal mucosa.

The dosage form provides sustained release of the antiviral active pharmaceutical ingredient(s) while incorporating mucoadhesion properties on the vaginal or rectal wall, limiting the inconvenience in the user, and providing sustained release. The dosage form is typically for local topical administration. The application of the dosage form can be performed by the user. In accordance with certain embodiments, the dosage form is referred to an insert since the dosage form is inserted into the vaginal or rectal cavity.

Examples of active pharmaceutical ingredients include, but are not limited to, antivirals (entry inhibitors, fusion inhibitors, nucleoside analog reverse-transcriptase inhibitors [NRTIs], nucleotide analog reverse-transcriptase inhibitors [NtRTIs], non-nucleoside reverse-transcriptase inhibitors [NNRTIs], integrase inhibitors, protease inhibitors, capsid inhibitors and large molecule biologics including, but not limited to, DNA/RNA, antibody, protein, peptide and adeno-associated virus [AAV] vector, large molecule biologics/ excipients lyophilized dry blend), antibacterial agents, antifungal agents, spermicides, hormones, contraceptive agents, micronutrients (such as vitamins, minerals) and/or combinations thereof. In accordance with certain embodiments, the dosage forms may also contain an antibiotic to prevent sexually transmitted infections (STIs) or genital or rectal infections, such as those caused by bacterial vaginosis, trichomoniasis, and syphilis *chlamydia*, gonorrhea and *treponema* species in addition to viral infections caused by HIV, HSV and HBV. Examples of useful antibiotics include, but are not limited to, tetracyclines, macrolides, nitroimidazoles and lincosamides. Antibiotics that may be particularly useful include doxycycline, in the form of doxycycline hyclate or doxycycline anhydrous or doxycycline monohydrate, azithromycin, metronidazole, tinadazole, secnidazole, and clindamycin.

In accordance with some embodiments, the dosage form contains a combination of antiviral drugs and, in some cases, a combination of (a) an NRTI and (b) an integrase inhibitor. Examples of NRTI's include, but are not limited to, adefovir, adefovir dipivoxil, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, abacavir, abacavir sulfate, alovudine, apricitabine, censavudine, didanosine, elvucitabine, festinavir, fosalvudine tidoxil, fozivudine tidoxil, lamivudine, phosphazid, stavudine, zalcitabine, and zidovudine. Examples of integrase inhibitors include, but are not limited to, elvitegravir, curcumin, chicoric acid, 3,5-dicaffeoylquinic acid, aurintricarboxylic acid, caffeic acid phenethyl ester, tyrphostin, quercetin, raltegravir, dolutegravir, cabotegravir and derivatives thereof.

In accordance with particular embodiments, the dosage form contains a combination of (a) Tenofovir Alafenamide and (b) Elvitegravir (EVG). In certain embodiments, the Tenofovir Alafenamide is in the Fumarate (TAF) salt form. In accordance with certain embodiments, the dosage form may also contain an antibiotic in addition to TAF and EVG.

In accordance with some embodiments, the dosage form may contain from about 1.5% to about 15% by weight of active pharmaceutical ingredients and more particularly from about 2% to about 10% of the active pharmaceutical ingredients. In accordance with some embodiments, the dosage form may contain a combination of active pharmaceutical ingredients wherein each individual active pharmaceutical ingredient is present in an amount from about 1% to about 12%, more particularly from about 2% to about 8% and still more particularly from about 1.6% to about 4.8% by weight. In accordance with certain embodiments, the dosage form contains a combination of (a) Tenofovir Alafenamide Fumarate (TAF) salt form and (b) Elvitegravir (EVG). In some embodiments, the dosage form may contain tenofovir alafenamide fumarate (TAF) in an amount ranging from about 2% to about 8% TAF as free base (equivalent to 2.24% to 8.96% of Tenofovir alafenamide fumarate salt basis) and about 1.6% to about 4.8% elvitegravir (EVG).

Antibiotics, when included in the dosage form, may be used in amounts sufficient to obtain the desired therapeutic effect. Typically, the antibiotics may be included in an amount from about 2% to 30%, more particularly from about 5% to 25%, and in certain cases from about 10% to 20% by weight of the dosage form.

The dosage forms described herein may contain a combination of pharmaceutically acceptable carriers and/or excipients that provide for the desired mucoadhesive properties and sustained release of the active. Typically used excipients include, but are not limited to, binders, bioadhesive polymers, disintegrating agents, diluents, bulking agents, hydrophilic excipients and lubricants. Some excipients can provide one or more functional roles in the dosage form.

Examples of binders include, but are not limited to, povidone (polyvinylpyrrolidone, PVP), sodium carboxymethylcellulose (NaCMC), carboxymethyl cellulose (CMC), starch, hydroxypropylmethyl cellulose (HPMC), carboxymethyl cellulose (CMC), hydroxypropyl cellulose (HPC), acacia, tragacanth and gelatin. In accordance with certain embodiments, the binder is a povidone, such as povidone K29/32, povidone K30, povidone K90, povidone K15, povidone K17 PF, and povidone K25. Combinations of binders can also be used. In accordance with certain embodiments, the binder is also a bioadhesive polymer, which contributes to the mucoadhesive properties of the dosage form. In accordance with some embodiments, the binder also functions as a disintegrant. In accordance with certain embodiments, the binder may be present in an amount from about 0.5% to 8%, more particularly from about 1% to 5%, and in certain cases from about 2% to 4% by weight of the dosage form.

Examples of bioadhesive polymers include, but are not limited to, hyaluronic acid, sodium hyaluronate, carrageenan and sodium alginate and PEG. In accordance with certain embodiments, the bioadhesive polymer is a PEG and more particularly PEG 6000 or PEG 8000. Combinations of bioadhesive polymers can also be used. In accordance with certain embodiments, the bioadhesive polymer may be present in an amount from about 5% to 30%, more particularly from about 7.5% to 25%, and in certain cases from about 10% to 20% by weight of the dosage form.

Examples of disintegrating agents include, but are not limited to, starch, sodium starch glycolate, povidone and calcium silicate, polysorbates (such as polysorbate 20 or 80), and poloxamers (such as poloxamer 188 or 207). In a particular embodiment, the disintegrating agent is a poloxamer, more particularly poloxamer 188. Combinations of disintegrating agents can also be used. In accordance with certain embodiments, the disintegrating agent is water soluble. In accordance with some embodiments, the dosage form is free of any water insoluble disintegrating agents and/or super disintegrants, such as crospovidone or croscarmellose. In accordance with certain embodiments, the disintegrating agent may be present in an amount from about 0.5% to 4%, more particularly from about 1% to 3%, and in certain cases from about 1.5% to 2.5% by weight of the dosage form.

Examples of lubricants include, but are not limited to, magnesium stearate, calcium stearate, stearic acid, glycerol monostearate, sodium stearyl fumarate, colloidal silicon dioxide, and talc. Combinations of lubricants can also be used. In accordance with certain embodiments, the lubricant may be present in an amount from about 0.2% to 4%, more particularly from about 0.5% to 3%, and in certain cases from about 1% to 2% by weight of the dosage form.

Examples of fillers (also known as bulking agents or diluents) include, but are not limited to, starches, maltodextrins, polyols (such as lactose), sugar alcohols and celluloses. Combinations of fillers can also be used. In accordance with certain embodiments, the filler may be present in an amount from about 5% to 90%, more particularly from about 10% to 75%, and in certain cases from about 20% to 60% by weight of the dosage form. Dosage forms provided herein may include lactose and/or sugar alcohols. Lactose can be used in anhydrous or hydrated form (e.g., monohydrate). In accordance with certain embodiments, lactose may be present in an amount from about 25% to 75%, more particularly from about 30% to 70%, and in certain cases from about 40% to 60% by weight of the dosage form. Examples of sugar alcohols that may be used include, but are not limited to, mannitol, glycerol, erythritol, xylitol, sorbitol, isomalt, maltitol, lactitol, and mixtures thereof. In accordance with certain embodiments, sugar alcohols may be present in an amount from about 5% to 30%, more particularly from about 7.5% to 25%, and in certain cases from about 10% to 20% by weight of the dosage form.

Examples of hydrophilic excipients include, but are not limited to, hyaluronic acid, maltodextrin, dextrin, cyclodextrin, Vitamin E TPGS, Pluronics, amino acids, gelatins, polyethylene glycols including, but not limited to, polyethylene glycol 4000 (PEG 4000), polyethylene glycol 6000 (PEG 6000), polyethylene glycol 8000 (PEG 8000), poly (ethylene oxide) (PEO), poly(vinylpyrrolidinone) (PVP), cellulose ethers including, but not limited to, hydroxypropylmethyl cellulose (HPMC), hydroxypropyl cellulose (HPC), hydroxyethyl cellulose (HEC), sodium carboxy methyl cellulose (Na CMC), methylcellulose (MC), and mixtures thereof. Combinations of hydrophilic excipients can also be used. In accordance with certain embodiments, the hydrophilic excipients may be present in an amount from about 0.5% to 25%, more particularly from about 10% to 20%, and in certain cases from about 5% to 15% by weight of the dosage form.

In accordance with some embodiments, the solid dosage form may have a weight of about 0.1 to about 2.0 gm, more particularly of about 0.2 to about 1.0 gm and still more particularly of about 0.25 to about 0.75 gm. In some cases, the nominal average weight may be about 0.5 gm (0.475 to 0.525 gm).

In accordance with some embodiments, the solid dosage form may have a length of about 10 mm to 25 mm, a width of about 5 mm to 20 mm, and a thickness of about 2 mm to 10 mm. The shape of the dosage form is not particularly limited, but the dosage form may be in the shape of a circle, oval, rectangle, square, triangle, capsule, bullet, diamond, or almond.

In accordance with some embodiments, the solid dosage form has a pH of 3 to 7.5 after dissolution in 0.5 to 10 ml volume of water and is compatible with the pH of vaginal and rectal compartment upon dissolving.

Although the present application exemplifies solid dosage forms, other dosage forms such as gels, foams, films, intravaginal rings, douches, enema, suppositories, tablets, transdermal patches, suspension, emulsion, pessaries may also be useful. In accordance with certain embodiments, the dosage forms provide for topical administration of the active pharmaceutical ingredient. Particularly useful compositions are those in which a tenofovir prodrug is combined with an integrase inhibitor and more particularly wherein TAF is combined with EVG or TAF is combined with other integrase inhibitors such dolutegravir and cabotegravir as well as with prodrugs of integrase inhibitors.

Methods of Use

The compositions and dosage forms disclosed herein can be used in the treatment and/or prevention of various diseases, such as HIV, HSV and HBV. In certain embodiments, a method for treating or preventing a viral infection in a subject comprises administering a pharmaceutical composition or solid dosage form as described herein to the subject. This present application discloses the potential benefits of combining TAF with EVG in a formulation such as vaginal or rectal insert for the prevention or treatment of HIV, HSV and HBV for both pre and post exposures. The effectiveness of the composition for the prevention or treatment of HIV, HSV and HBV for both pre and post exposures is unexpected and surprising. In some embodiments, a method for treating or preventing a viral infection as well as treating another infection, such as a bacterial or fungal infection, in a subject comprises administering a pharmaceutical composition in a solid dosage form as described herein to the subject. Infections than may be treated include, but are not limited to, *chlamydia*, gonorrhea, bacterial vaginosis, trichomoniasis, and syphilis.

Manufacturing Process

The solid dosage forms disclosed herein can be produced using conventional processing steps and manufacturing processes. One exemplary process for producing the solid dosage forms is provided below.

The API's can be passed through a screen (e.g., mesh #20) and charged into a blender, such as a V_SHEL/TOTE blender. The excipients can be screened (e.g., through a 045R screen and round impeller at approximately 1250 rpm) and then charged into the blender. The components can be mixed for a period of time and then discharged into a polyethylene lined container. Then, the blend can be transferred to a tablet press for slugging. The slugs are then collected into a polyethylene lined container and samples tested for weight, thickness and hardness. The slugged material can then be passed through a screen (e.g., through a 045R screen and round impeller at approximately 1250 rpm) and then the approximately one half of the slugged material is charged into the blender. The lubricant and any remaining ingredients are charged into the blender and then the remaining one half of the slugged material is charged into the blender. The resulting blend is mixed, sampled and then discharged into a polyethylene lined container. The blend is introduced to a tablet press and samples tested for dissolution properties. The resulting solid dosage forms (inserts) are dedusted and screened before being collected into triple polyethylene lined pails adding two dessicant pads between the outer and inner polyethylene liner. The resulting inserts are retained and sampled for testing.

EXAMPLES

The following examples are presented for the purpose of illustration only and are not intended to be limiting.

Osmolality of TAF/EVG vaginal insert for placebo (no active drugs) and P02 (TAF/EVG 40/24 mg) and P03 (TAF/EVG 20/16 mg) was studied in Artificial Vaginal fluid at a pH of 4.2 and the results are summarized in Table 1 below indicating acceptable osmolality range.

TABLE 1

The osmolality of Placebo, P02 and P03 in the artificial vaginal fluid at different time intervals was measured and is presented below.

| Time | Placebo (mOsm/L) | PO2 (mOsm/L) | PO3 (mOsm/L) |
|---|---|---|---|
| 0 | 212 | 212 | 213 |
| 15 | 541 | 425 | 464 |
| 30 | 785 | 491 | 639 |
| 45 | 882 | 635 | 772 |
| 60 | 1062 | 560 | 664 |

Table 2 below provides exemplary formulations containing two antiviral drugs: Tenofovir alafenamide and elvitegravir. Three formulation compositions of TAF/EVG Insert (F1, F2 and F3) were manufactured and met hardness, friability and in vitro release in simulated vaginal fluid criteria. Hardness values are typically in the range of 5-8. Friability is typically less than 1.0%. The appearance of the dosage form in this example was white to off-white uncoated bullet shaped insert.

TABLE 2

Manufacturing Process Examples (F1-F3 formulations in three strengths)

| | | Formulation ID | | | | |
|---|---|---|---|---|---|---|
| | | F1 | | F2 | | F3 | |
| Ingredients | % | Weight (mg) | % | Weight (mg) | % | Weight (mg) |
| 1 Tenofovir Alafenamide Fumarate (TAF) | 8.96 | 44.8* | 4.48 | 22.4** | 2.24 | 11.2** |
| 2 Elvitegravir (EVG) | 4.8 | 24 | 3.2 | 16 | 1.6 | 8 |

TABLE 2-continued

Manufacturing Process Examples (F1-F3 formulations in three strengths)

| | Formulation ID | | | | | |
|---|---|---|---|---|---|---|
| | F1 | | F2 | | F3 | |
| Ingredients | % | Weight (mg) | % | Weight (mg) | % | Weight (mg) |
| 2 Povidone (K-29/32) | 4 | 20 | 4 | 20 | 2 | 10 |
| 4 Magnesium Stearate | 1 | 5 | 1 | 5 | 0.5 | 2.5 |
| 5 Poloxamer 188 | 2 | 10 | 2 | 10 | 1 | 5 |
| 6 Lactose monohydrate | 49.88 | 249.4 | 52.92 | 264.6 | 26.46 | 132.3 |
| 7 Mannitol | 14.36 | 71.8 | 17.4 | 87 | 8.7 | 43.5 |
| 8 PEG 8000 | 15 | 75 | 15 | 75 | 7.5 | 37.5 |
| Total | 100 | 500* | 100 | 500* | 100 | 500* |

*Equivalent to 40.0 mg of Tenofovir Alafenamide free base (F1)
**Equivalent to 20.0 mg of Tenofovir Alafenamide free base (F2)
***Equivalent to 10.0 mg of Tenofovir Alafenamide free base (F3)

Figure 1B:
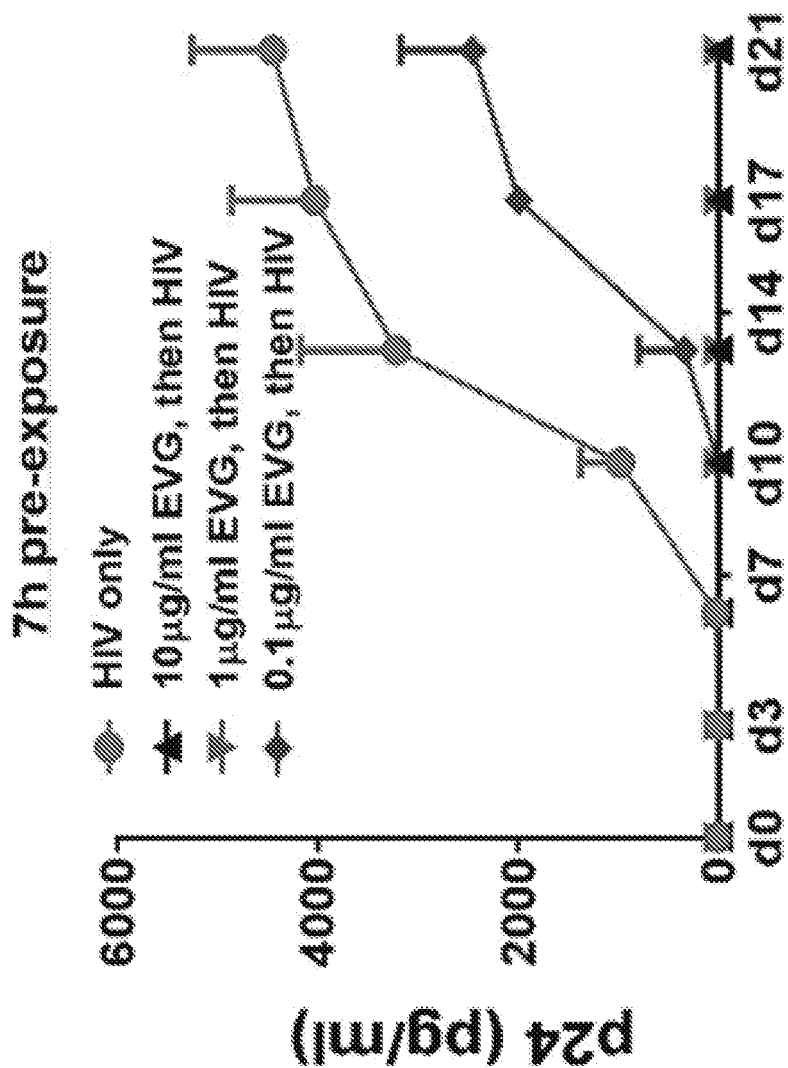
Figure 1C:
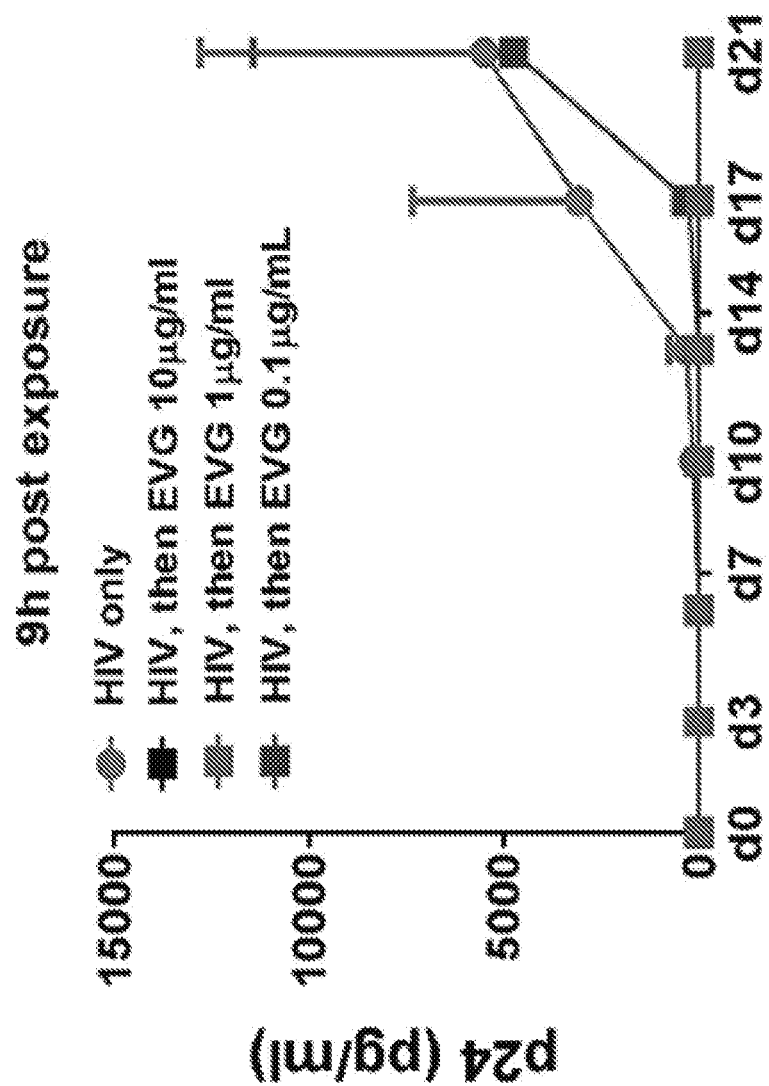

EVG demonstrated potent anti-HIV activity in cervical vaginal (CV) tissue explant study when applied up to 24 hours pre-or post-HIV exposure. The antiviral effect was dose-dependent, with 1 and 10 µg/mL EVG doses provided complete protection at all pre and post exposure time points, and at 0.1 µg/mL EVG appeared to be unable to fully protect against HIV in the pre-exposure settings as presented in Table 3 and FIG. 1.

TABLE 3

Mean percentage of protection of EVG against HIV infection

| % protection of mean AUC | | EVG concentration | | |
|---|---|---|---|---|
| versus HIV control | | 0.1 µg/ml | 1 µg/ml | 10 µg/ml |
| Pre-exposure | 0 h | 34.5% | 99.97% | 100% |
| | 7 h | 21.53% | 99.1% | 100% |
| | 24 h | 44.8% | 99.51% | 100% |
| Post-exposure | 4 h | 86% | 99.56% | 100% |
| | 9 h | 85.85% | 100% | 100% |
| | 14 h | NT | NT | 100% |
| | 24 h | NT | NT | 100% |
| Co-exposure virus and EVG | virus and API added together | 97.56% | 100% | NT |

Percent of protection determined from explants of 3-9 donors using the following equation:
100 − (AUC treated explants*100/AUC untreated explants).
AUC: area under the infection curve.
NT: not tested.

Figure 2:
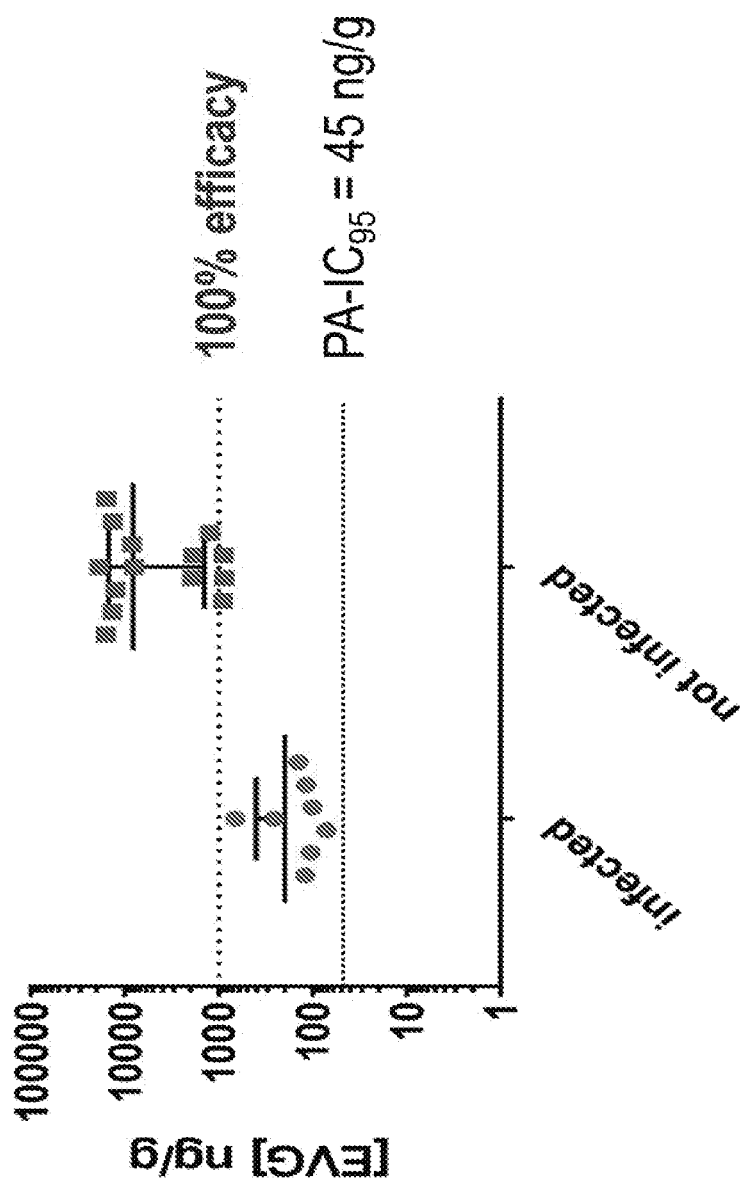
FIG. 2 is a graph showing EVG concentrations in infected vs. not infected CV tissues. Median concentrations and ranges (min and max) are shown. PA=Protein adjusted.

The median EVG concentration in CV tissues following 4 h of exposure to 10 and 1 µg/ml of EVG, both of which completely inhibited HIV infection in CV explant tissues were: 13,381 ng/g and 1150 ng/g, respectively. Based on the data, it can be extrapolated that EVG tissue concentrations of >1000 ng/g provided 100% HIV prophylaxis. (FIG. 2).

Figure 3:
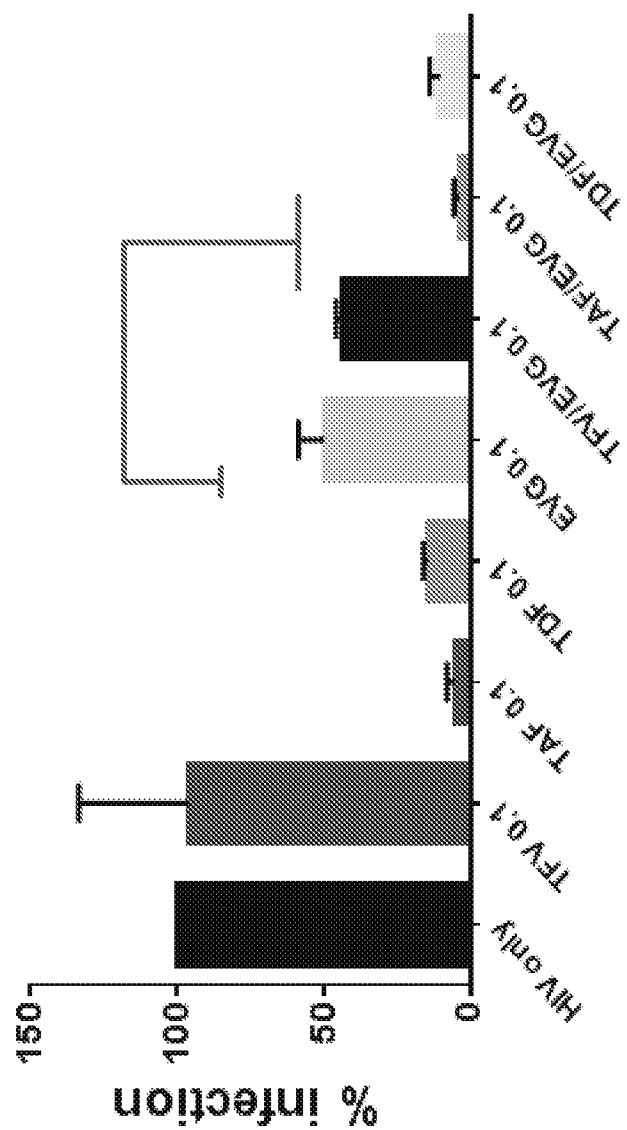
FIG. 3 is a bar chart showing activity of various anti-viral drugs at pre-exposure (−24 hours).
Figure 4:
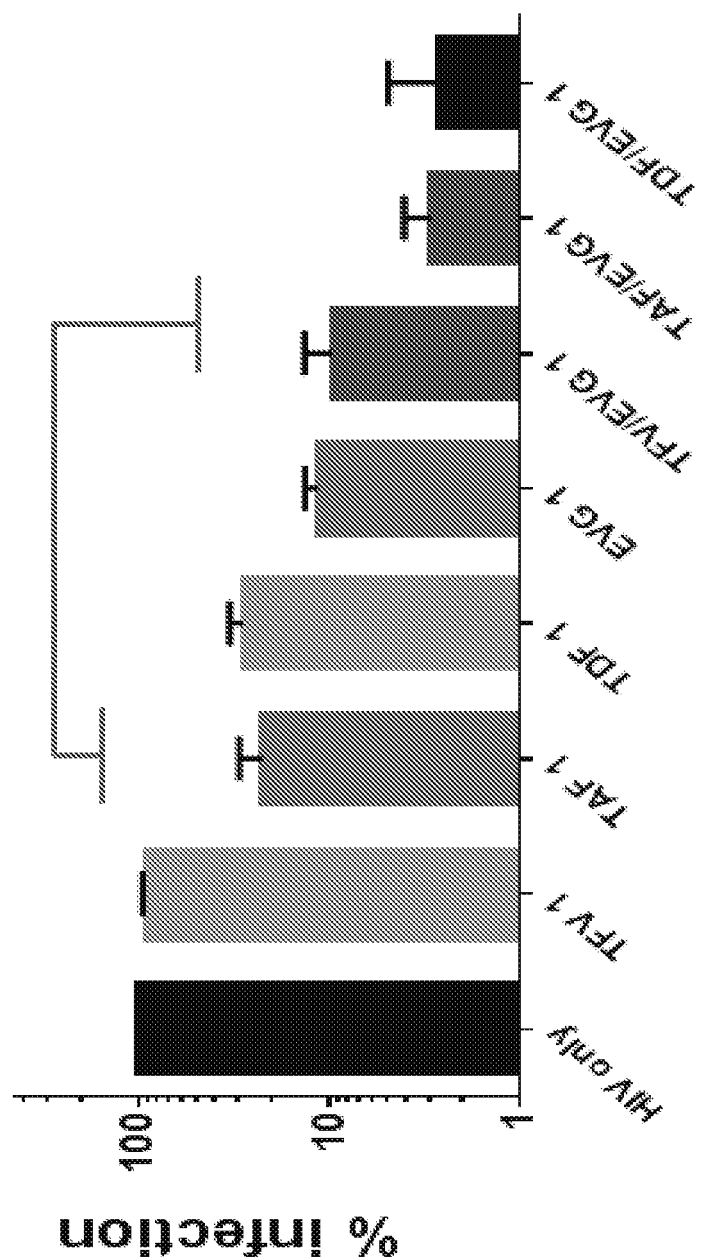
FIG. 4 is a bar chart showing activity of various anti-viral drugs at post-exposure (+6 hours).

The present application provides solid dosage forms in which all forms of tenofovir pro drugs (e.g., tenofovir disoproxil fumarate (TDF); tenofovir alafenamide fumarate (TAF)) can be used either alone or in combination with integrase inhibitor such as EVG. These tenofovir prodrugs in in vitro cell model studies showed improved potency pre HIV exposure (FIG. 3) and post HIV exposure (FIG. 4) when combined with EVG, thereby demonstrating that an expanded window of prophylactic activity can be obtained by combining tenofovir pro drug and EVG. Infection was significantly lower for combination of TAF combined with EVG and TDF combined with EVG in both pre and post HIV exposure.

Figure 5:
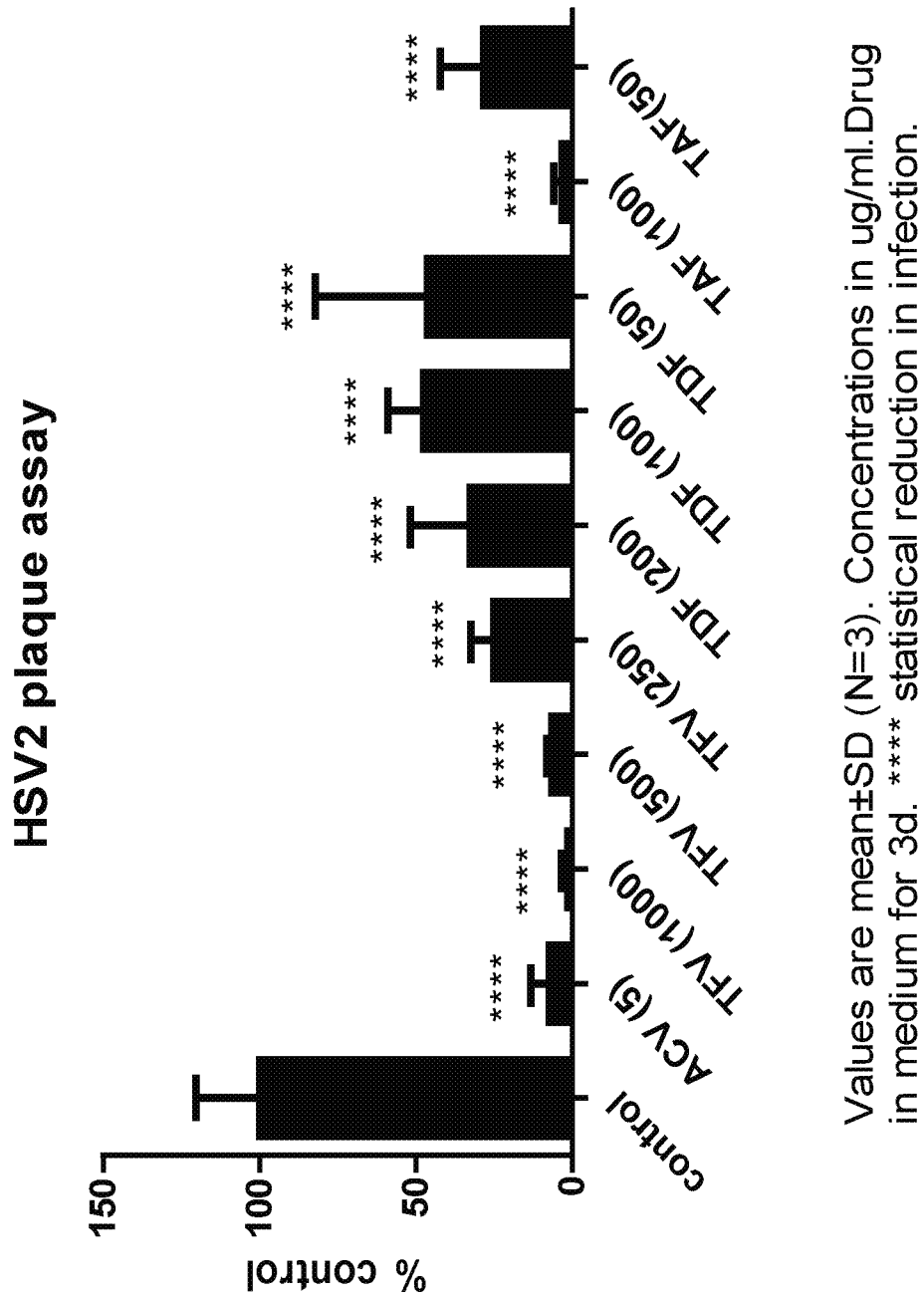
FIG. 5 is a bar chart showing anti-HSV activity for prevention of genital herpes with various tenofovir prodrugs.

TAF, TFV, acyclovir (ACV), TDF were found to show improved activity against HSV. TFV and TFV prodrugs display anti-HSV activity and TAF was found to be the most potent (FIG. 5)

TAF/EVG 20/16 mg insert is a stable product as demonstrated by 6 months stability at 30° C./75% RH and 40° C./75% RH for the lead formulation containing TAF/EVG (20/16 mg) (P03) with 3 g of silica gel desiccants in HDPE bottles containing 20 inserts in each. The results are summarized in Table 4 and Table 5.

TABLE 4

Stability of TAF/EVG Insert 20/16 mg Pilot Batch (P03 - 30° C./65% RH)

| Parameters | T = 0M | T = 1M | T = 3M | T = 6M |
|---|---|---|---|---|
| Physical Appearance (n = 10) | Pass | Pass | Pass | Pass |
| Hardness (kg) (n = 10) | 5.98 ± 0.34 | 5.86 ± 0.51 | 4.58 ± 0.55 | 6.01 ± 0.49 |
| Friability (%) (n = 13) | 0.58 | 0.33 | 0.55 | 0.49 |
| Content Assay (%) -TAF (n = 10) Target (90-110.0%) | 97.36 ± 0.78 | 102.40 ± 0.58 | 102.87 ± 0.49 | 91.41 ± 0.69 |
| Content Assay (%) -EVG (n = 10) Target (90-110.0%) | 95.97 ± 0.39 | 100.82 ± 0.42 | 97.84 ± 0.95 | 95.53 ± 1.95 |
| RC (%)* (n = 10) | ND** | ND** | ND** | ND** |
| Moisture Content (%) (n = 5) | 0.20 ± 0.02 | 0.02 ± 0.00 | 0.68 ± 0.16 | 0.19 ± 0.00 |
| Dissolution (Client) (min) (n = 6) | 60 | 60 | 60 | 60 |
| Disintegration (min) (n = 6) | 15 | 15 | 20 | 14 |

*RC (%): Total impurities (related compounds, RC1, RC2, and RC3).
**ND: Not Detectable.

TABLE 5

| Stability of TAF/EVG20/16 mg insert Pilot Batch (P03 - 40° C./75% RH) | | | | | |
|---|---|---|---|---|---|
| Parameters | T = 0M | T = 1M | T = 2M | T = 3M | T = 6M |
| Physical Appearance (n = 10) | Pass | Pass | Pass | Pass | Pass |
| Hardness (kg) (n = 10) | 5.98 ± 0.34 | 5.75 ± 0.42 | 5.74 ± 0.41 | 6.42 ± 0.85 | 6.01 ± 0.60 |
| Friability (%) (n = 13) | 0.58 | 0.8 | 0.51 | 0.65 | 0.65 |
| Content Assay (%) -TAF (n = 10) | 97.36 ± 0.78 | 100.28 ± 1.02 | 102.00 ± 0.77 | 98.20 ± 1.60 | 94.00 ± 0.74 |
| Content Assay (%) -EVG (n = 10) | 95.97 ± 0.39 | 100.57 ± 0.47 | 100.12 ± 0.40 | 93.98 ± 0.78 | 94.58 ± 0.30 |
| RC (%)* (n = 10) | ND** | ND** | ND** | ND** | ND** |
| Moisture Content (%) (n = 5) | 0.20 ± 0.02 | 0.05 ± 0.02 | 0.07 ± 0.02 | 0.29 ± 0.18 | 0.17 ± 0.00 |
| Dissolution (Client) (min) (n = 6) | 60 | 60 | 60 | 60 | 60 |
| Disintegration (min) (n = 6) | 15 | 16 | 15 | 20 | 25 |

*RC (%): Total impurities (related compounds, RC1, RC2, and RC3).
**ND: Not Detectable.

Stability Testing

Figure 6:
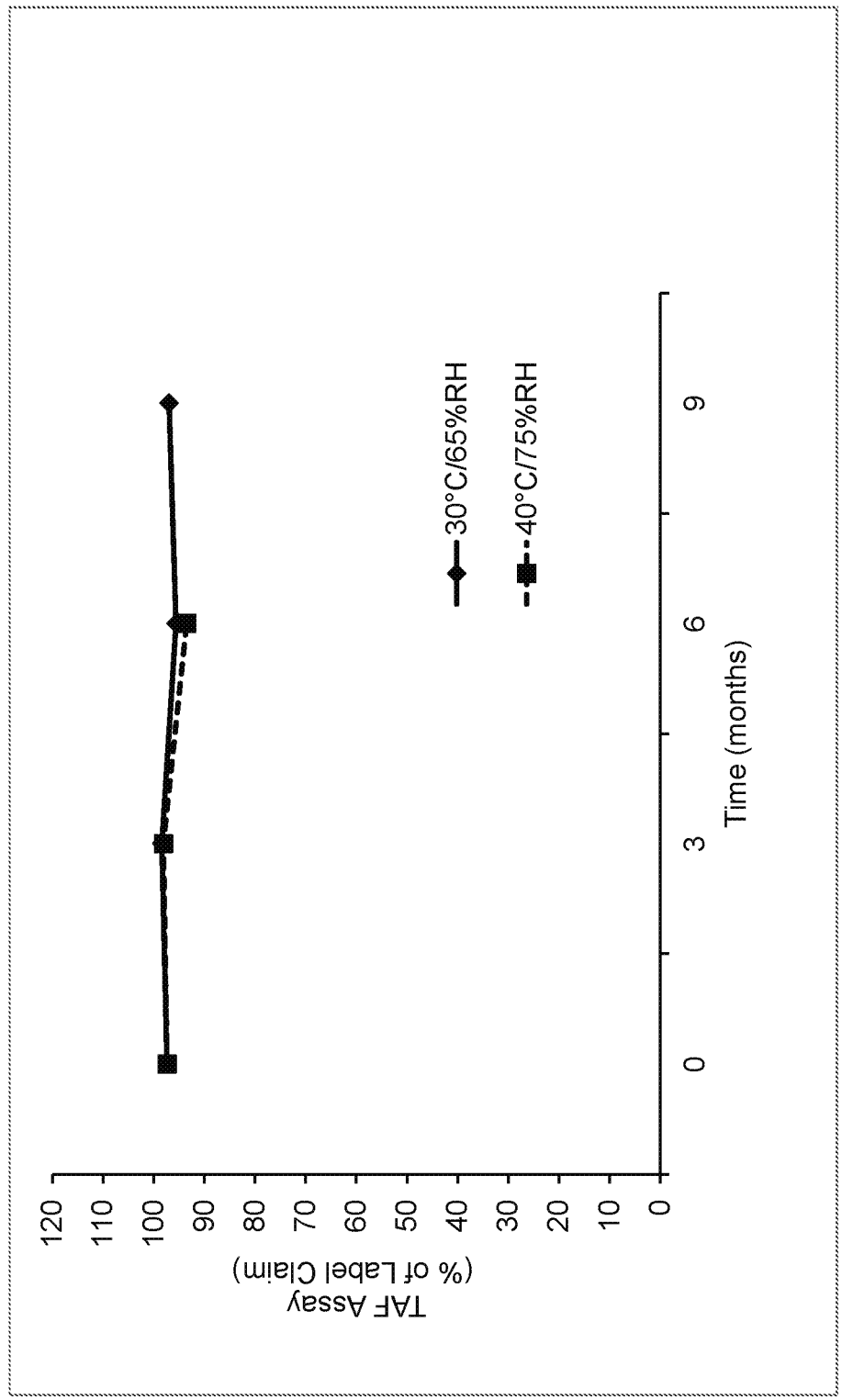
FIG. 6 is a graph showing Tenofovir Alafenamide (TAF) Assay (% of Label Claim) in TAF/EVG 20/16 mg Insert on Stability at 30° C./65% RH (up to 9 months) and at 40° C./75% RH (up to 6 months).
Figure 7:
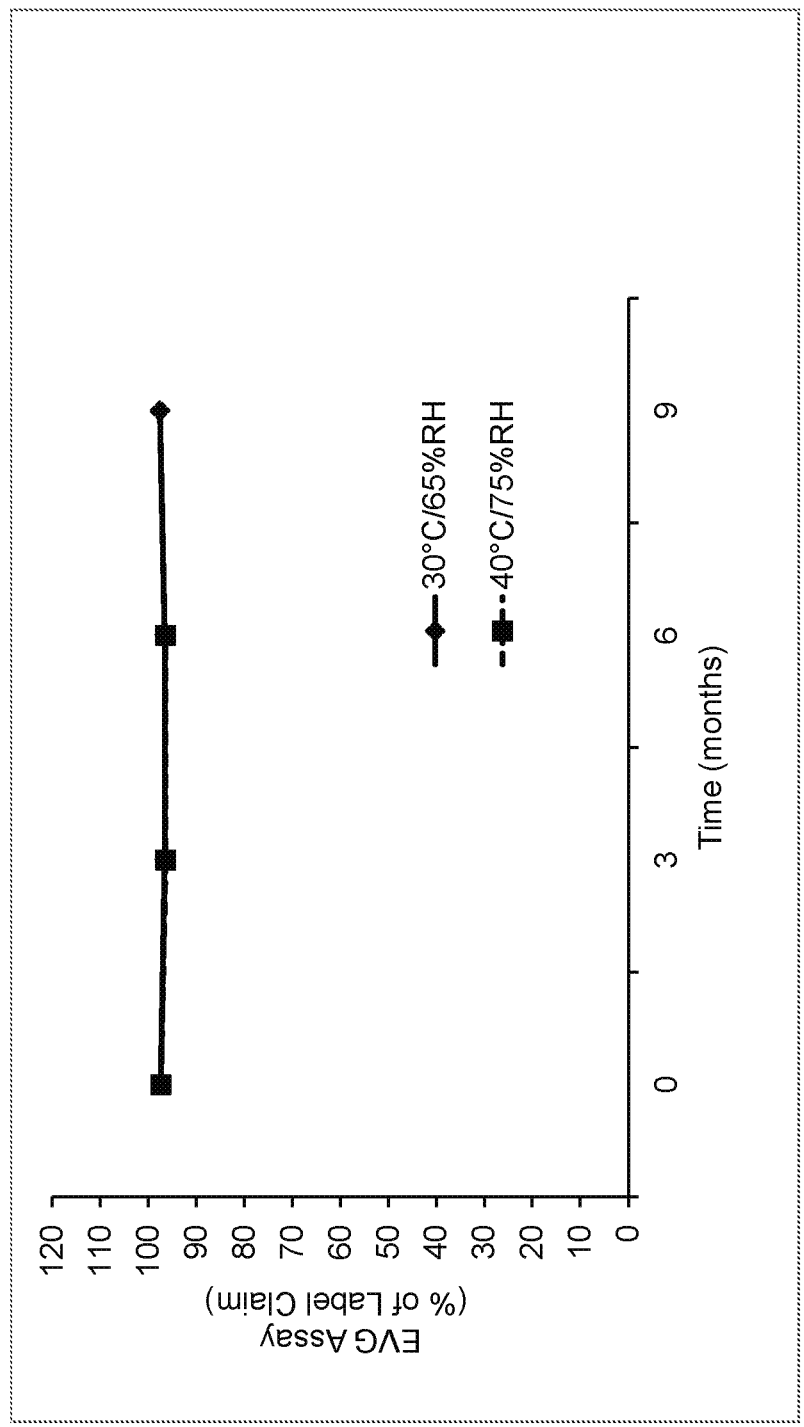
FIG. 7 is a graph showing Elvitegravir (EVG) Assay (% of Label Claim) in TAF/EVG 20/16 mg Insert on Stability at 30° C./65% RH (up to 9 months) and at 40° C./75% RH (up to 6 months).
Figure 8:
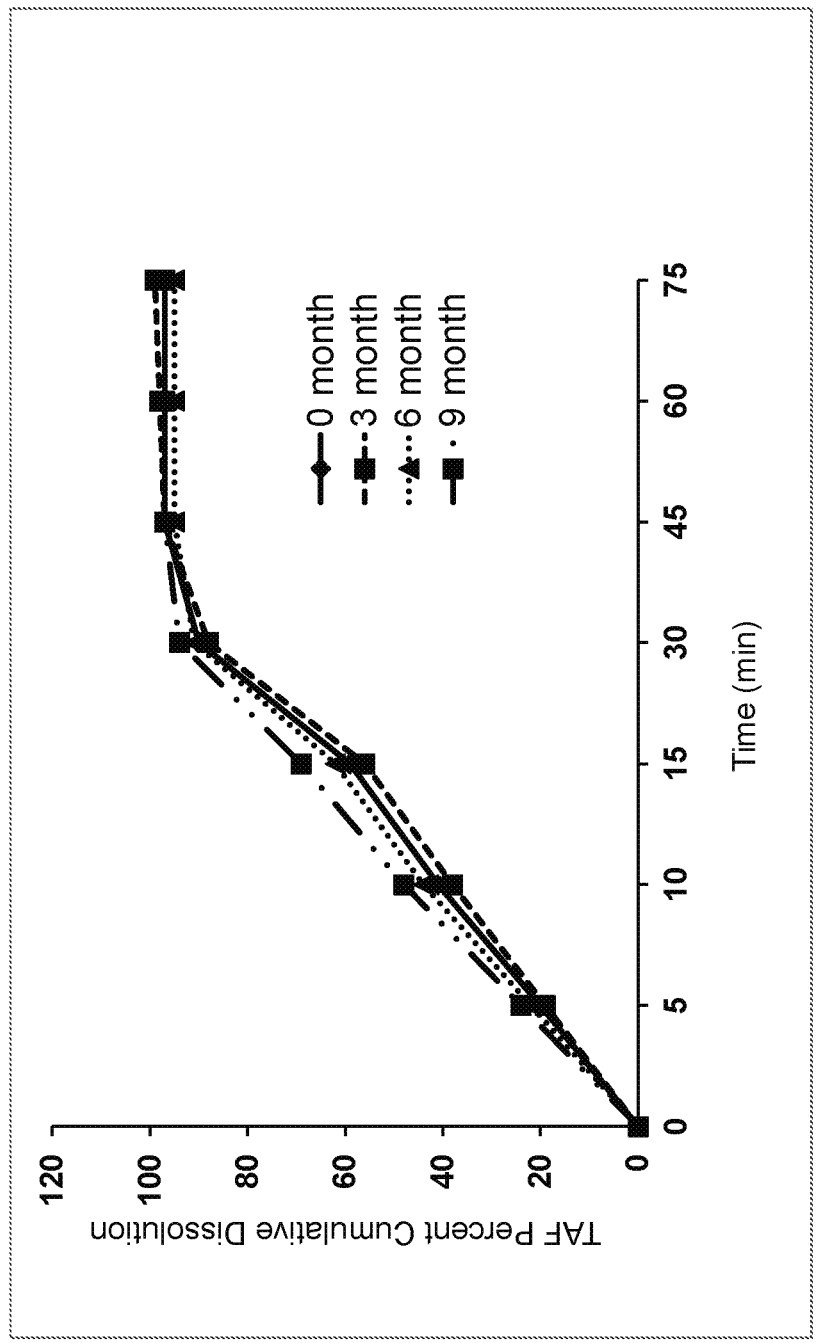
FIG. 8 is a graph showing Tenofovir Alafenamide (TAF) Percent Cumulative Dissolution in TAF/EVG 20/16 mg Insert on Stability at 30° C./65% RH (up to 9 months).
Figure 9:
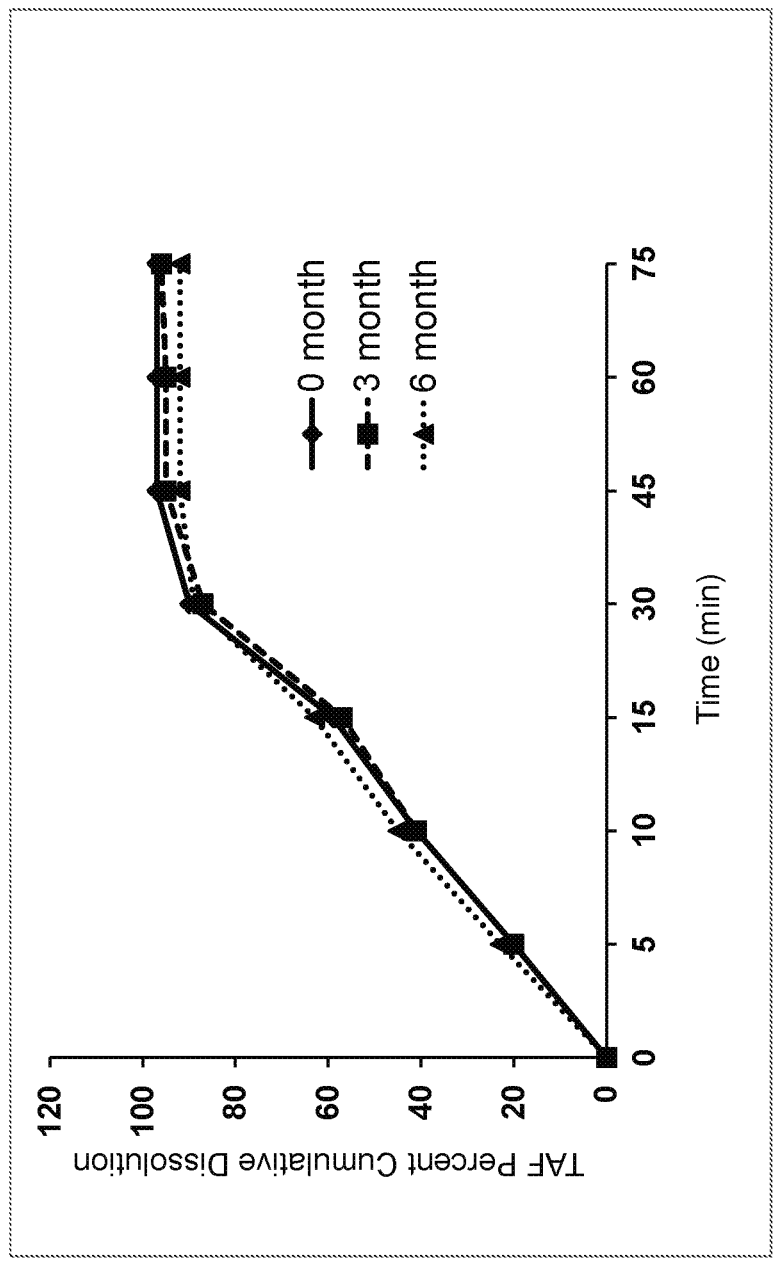
FIG. 9 is a graph showing Tenofovir Alafenamide (TAF) Percent Cumulative Dissolution in TAF/EVG 20/16 mg Insert on Stability at 40° C./75% RH (up to 6 months).
Figure 10:
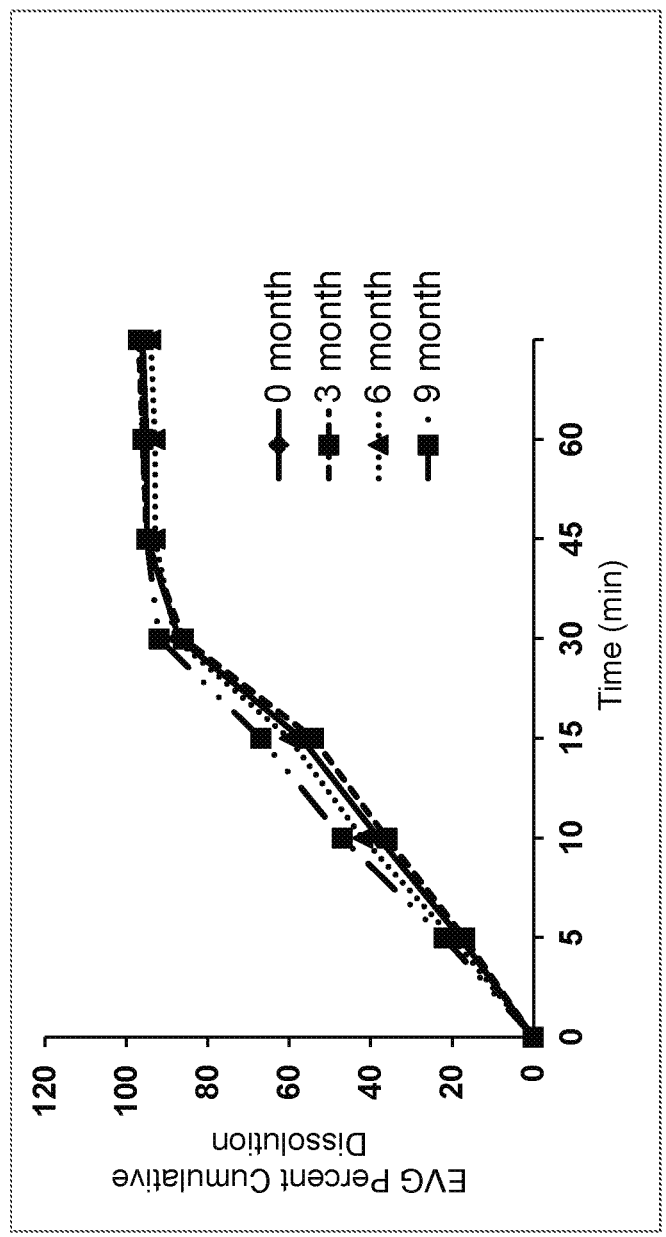
FIG. 10 is a graph showing Elvitegravir (EVG) Percent Cumulative Dissolution in TAF/EVG 20/16 mg Insert on Stability at 30° C./65% RH (up to 9 months).
Figure 11:
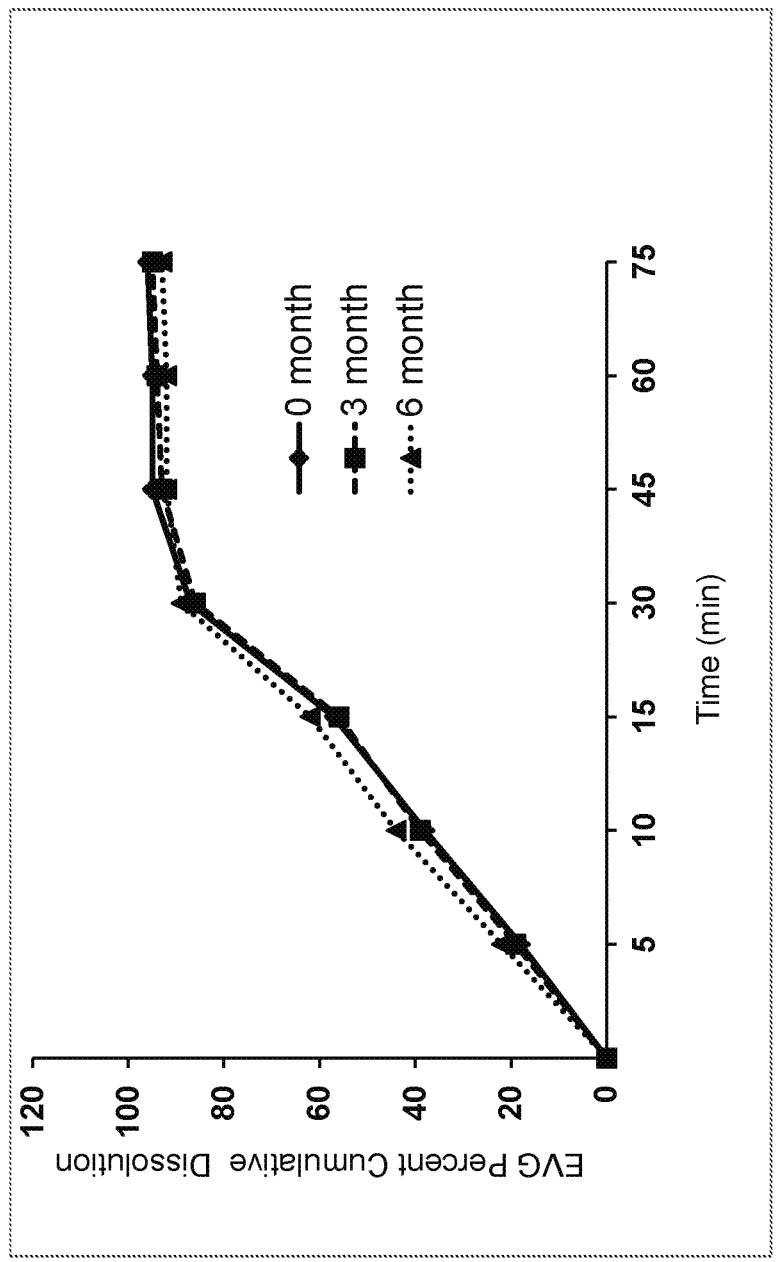
FIG. 11 is a graph showing Elvitegravir (EVG) Percent Cumulative Dissolution in TAF/EVG 20/16 mg Insert on Stability at 40° C./75% RH (up to 6 months).

TAF/EVG insert demonstrates excellent stability at both 30° C. and 40° C. and is expected to have minimum of two years shelf life when stored at or below 30° C. (see FIGS. 6 and 7). The stability of the TAF in the disclosed formulation is particularly unexpected in view of the drug typically being prone to degradation over time.

Percent Cumulative Dissolution Study of TAF/EVG Inserts

Dissolution of TAF/EVG insert was conducted using USP apparatus 2 (Paddle). The method consisted of six dissolution vessels. For this, six inserts were weighed, and individual inserts' weights were recorded. Each insert was placed into a stainless sinker and put into corresponding dissolution vessel and the timer was started immediately. Using a syringe fitted with a stainless steel cannula with a 10 μm full flow filter, a 5 mL portion of the solution was withdrawn from each vessel from a zone midway between the surface of the dissolution medium and the top of the paddle, not less than 1 cm from the vessel wall at 5, 10, 15, 30, 45, 60 minutes and infinity (additional 15 min at 250 rpm) time points and injected into the HPLC column after dilution using diluent. For the preparation of one liter of diluent, 500 mL of mobile phase A was added into 500 mL of acetonitrile (ACN) (mobile phase B), mixed well and degassed prior to use. A gradient method consisting of mobile phase A (20 mM Phosphate Buffer pH 2.5) and mobile phase B (100% ACN) was used. The following HPLC and dissolution method parameters were used to analyze the percent dissolution of tenofovir alafenamide and envitegravir from TAF/EVG inserts stored under stability conditions of 30° C./65% RH (at 0, 3, 6, and 9 months) and 40° C./75% RH (at 0, 3, and 6 months).

HPLC Parameters
    Column: Phenomenex Kinetex C-18, 4.6×150 mm, 2.6 μm, or equivalent
        Column Temperature: 30° C. Detection:
        UV @ 260 nm
        Injection Volume:10 μL
        Flow Rate: 1.2 ml/min
        Run Time: 16 minutes
        Mobile Phase A: 20 mM $KH_2PO_4$ in Water, pH 2.5
        Mobile Phase B:100% Acetonitrile
Dissolution Apparatus Parameters
    Apparatus: USP apparatus 2 (Paddle)
    Dissolution Temperature: 37.0±0.5° C.
    Rotation Speed: 50 rpm
    Dissolution Volume: 900
    Dissolution Medium: 50 mM phosphate buffer/0.25% SDS (pH=6.0)

TAF/EVG insert dissolution profiles of various samples aged on stability showed similar dissolution for TAF and EVG drugs compared to time zero, further establishing potential benefits of formulations produced in accordance with the present for HIV prevention (see FIGS. 8 to 11).

Mucoadhesive Properties

Figure 12:
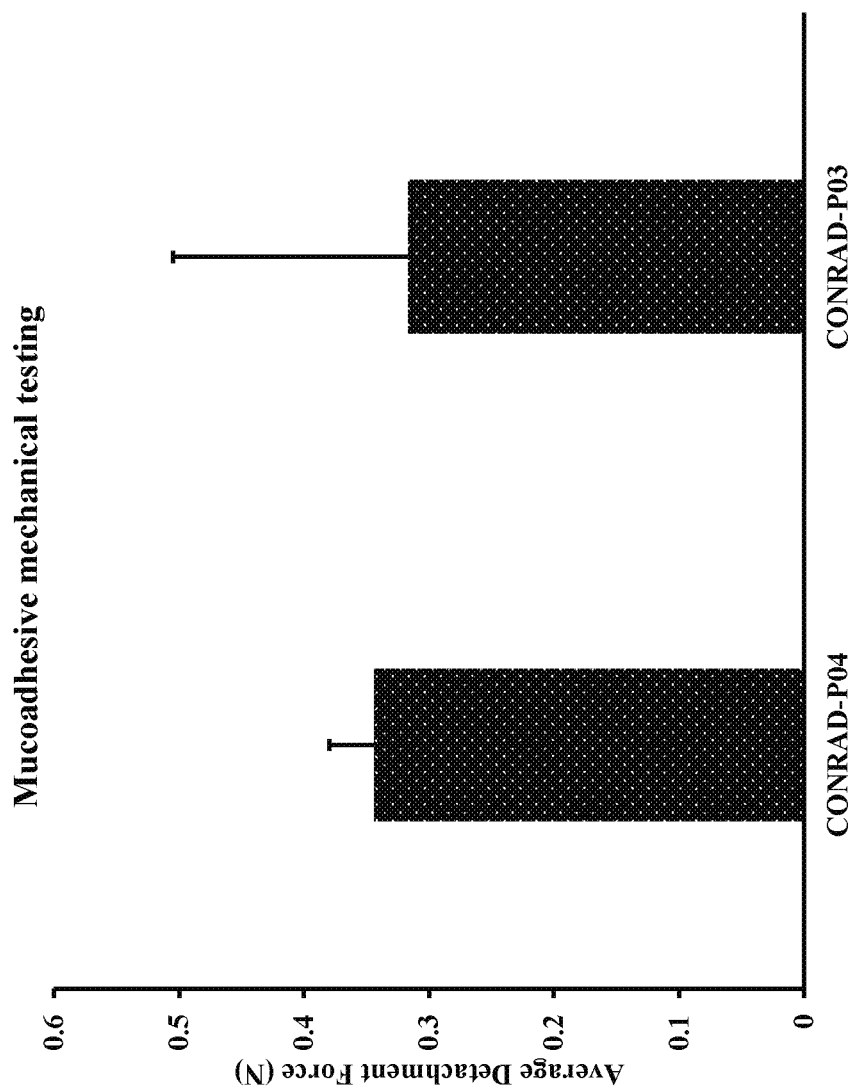
FIG. 12 is a bar chart showing the average detachment force of CONRAD-P04 (Placebo inserts) and CONRAD-P03 (TAF/EVG-20/16 mg inserts) from porcine vaginal tissue by mechanical test.

The bioadhesive properties were evaluated using porcine vaginal tissues by measuring the detachment force [(Table 6 and FIG. 12), and compared to the mucin solution as a control (Table 7 and Table 8)]. The detachment force of ~0.3 N (300 mN) for a dosage form insert with the porcine vaginal tissue vs ~0.01 N (10 mN) detachment force of insert with mucin solution shows a significant difference, thus the dosage form insert disclosed herein shows strong mucoadhesive properties. The mucoadhesive properties of the TAF/EVG insert with porcine vaginal mucosa were studied by Mechanical Testing method as briefly described below:

The mechanical testing apparatus consisted of two flat metal plates connected to a load cell, capable of measuring crush/tensile strength of values up to 50 Newton (N). A tablet die of a diameter comparable to that of the sample was placed on the bottom plate of the mechanical testing apparatus. A small segment of porcine vaginal tissue (2×2 cm) was attached to the top metal plate with cyanoacrylate adhesive and soaked in 50 mL of SVF for 30 seconds prior to the analysis. The test sample was tightly mounted inside the tablet die cavity. The insert was wetted by adding dropwise 50 μL of SVF using pipette and the upper portion of mechanical tester was lowered manually close enough to the insert and then lowered automatically at the rate of 5 mm/min (~0.1 mm/sec) to enable contact with the wetted insert for 60 seconds with a 5N compression force. The force required to detach the vaginal tissue from the insert was measured as detachment force in Newton (N). The samples tested in this study were CONRAD P03 (TAF/EVG 20/16 mg insert) and CONRAD P04 (placebo insert).

TABLE 6

Mechanical Test and bioadhesion studies

| Sample Type | Sample | Plate Tare Wt. (g) | Tissue Wt (dry) (g) | In Newton (N) | Detachment Force (N) | Detachment force - Tissue Wt force (N) | Average Detachment force - tissue Wt force (N) |
|---|---|---|---|---|---|---|---|
| CONRAD-P04 | P04-1 | 21.486 | 0.995 | 0.010 | 0.383 | 0.373 | 0.344 ± 0.036 |
| (Placebo | P04-2 | 21.482 | 0.533 | 0.005 | 0.308 | 0.303 | |
| Insert) | P04-3 | 21.482 | 0.854 | 0.008 | 0.363 | 0.355 | |
| CONR P03 | P03-1 | 21.482 | 0.650 | 0.006 | 0.368 | 0.362 | 0.317 ± 0.188 |
| (TAF/EVG | P03-2 | 21.482 | 0.857 | 0.008 | 0.280 | 0.272 | |
| Insert) | P03-3 | 21.482 | 0.769 | 0.008 | 0.358 | 0.350 | |

The Mucoadhesive Properties of Mucin Solution were Evaluated as Described Below

Different concentrations of mucin solutions (20%, 10%, and 1.5% w/v) were prepared by dissolving the mucin powder in SVF under overnight stirring at 37° C. The mechanical testing apparatus was used to analyze the detachment force for this study. The samples tested in this study were CONRAD P03 (TAF/EVG 20/16 mg insert) and CONRAD P04 (placebo insert). Distilled water was used as a control for all three tests.

Test A: Immersing the Insert in the Mucin Solutions (20, 10 and 1.5% w/v) (n=3)—

The insert was completely immersed in the mucin solutions. The insert was attached with the upper portion of mechanical tester and it was lowered manually to enable contact with the liquid for 30 seconds. The detachment force was measured using the software (Shimadzu Trapezium2 Version 2.22c).

Test B: Insert Touching the Surface of the Mucin Solutions (20, 10 and 1.5% w/v) (n=3)—

The insert was touched the surface of the mucin solutions. The insert was attached with the upper portion of mechanical tester and it was lowered manually to enable contact with the liquid for 30 seconds. The detachment force was measured using the software (Shimadzu Trapezium2 Version 2.22c).

TABLE 7

Insert immersed in the mucin solutions

| Sample | Medium | Forces (N) | Average Force (N) |
|---|---|---|---|
| P03-1 | Water | 0.012 | 0.010 ± 0.004 |
| P03-2 | Water | 0.005 | |
| P03-3 | Water | 0.013 | |
| P03-1 | Mucin 1.5% | 0.011 | 0.014 ± 0.006 |
| P03-2 | Mucin 1.5% | 0.01 | |
| P03-3 | Mucin 1.5% | 0.02 | |
| P03-1 | Mucin 10% | 0.01 | 0.012 ± 0.004 |
| P03-2 | Mucin 10% | 0.009 | |
| P03-3 | Mucin 10% | 0.016 | |
| P03-1 | Mucin 20% | 0.013 | 0.013 ± 0.002 |
| P03-2 | Mucin 20% | 0.011 | |
| P03-3 | Mucin 20% | 0.014 | |

TABLE 8

Insert touching the surface of the mucin solutions

| Sample | Medium | Forces (N) | Average Force (N) |
|---|---|---|---|
| P03-1 | Water | 0.013 | 0.012 ± 0.008 |
| P03-2 | Water | 0.004 | |
| P03-3 | Water | 0.02 | |
| P03-1 | Mucin 1.5% | 0.01 | 0.011 ± 0.008 |
| P03-2 | Mucin 1.5% | 0.009 | |
| P03-3 | Mucin 1.5% | 0.014 | |
| P03-1 | Mucin 10% | 0.011 | 0.009 ± 0.002 |
| P03-2 | Mucin 10% | 0.009 | |
| P03-3 | Mucin 10% | 0.007 | |
| P03-1 | Mucin 20% | 0.011 | 0.010 ± 0.001 |
| P03-2 | Mucin 20% | 0.009 | |
| P03-3 | Mucin 20% | 0.009 | |

Based on the mucoadhesion experiments performed, TAF/EVG 20/16 mg inserts have demonstrated unexpectedly good mucoadhesive behavior.

Figure 13:
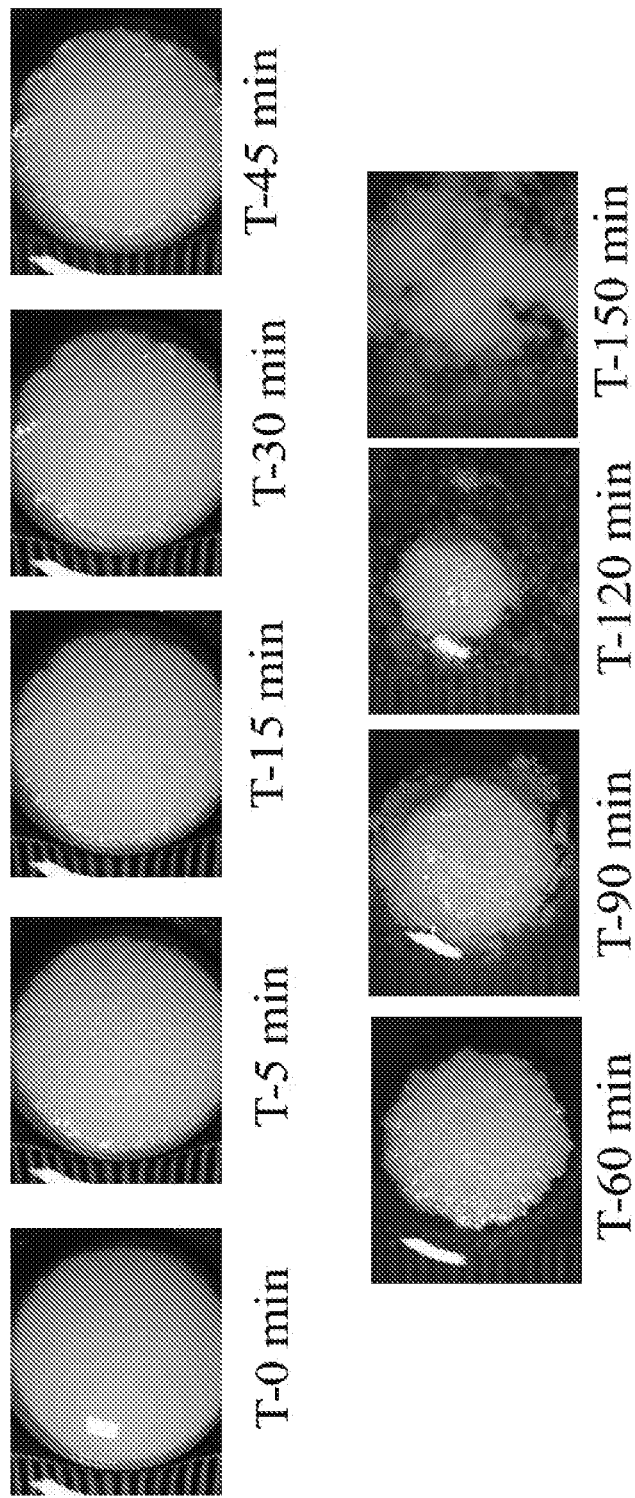
FIG. 13 illustrates dissolution and disintegration over time for an exemplary insert formulation (P03 (TAF/EVG-20/16 mg)) in Simulated Vaginal Fluid (SVF)-AC-3, pH 4.3 at 37° C.
Figure 14:
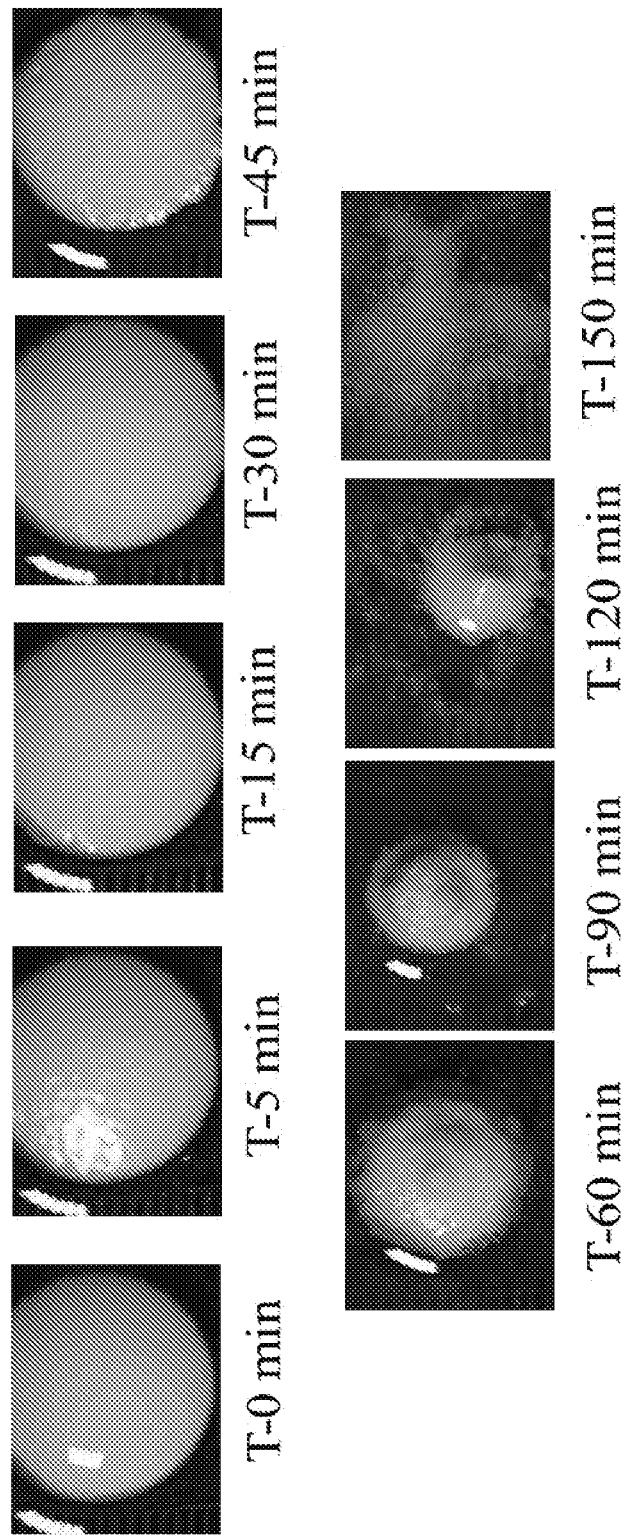
FIG. 14 illustrates dissolution and disintegration over time for an exemplary insert formulation (P03 (TAF/EVG-20/16 mg)) in PBS-AC-1, pH 4.3 at 37° C.

Additional data were also generated on dissolution and disintegration profiles for the dosage forms disclosed herein. The TAF/EVG 20/16 mg insert (CONRAD P-03) was evaluated for its disintegration/dissolution profiles by visual observation when exposed to 5 mL simulated vaginal fluid (SVF, pH 4.3 at 37° C.) and 5 mL simulated rectal fluid (phosphate buffered saline (PBS, pH 7.2 at 37° C.). Five mls of SVF or PBS (preheated at 37° C.) were added directly on top of the insert, and images were captured at predetermined time intervals of 0, 5, 15, 30, 45, 60, 90, 120 and 150 min, using a polarized AmScope Microscope Digital Camera (MU1000). In both SVF and PBS solution, dissolution/disintegration of the solid dosage form was driven by a surface erosion mechanism and the solid dosage form finally completely dissolved/disintegrated with no residue. The surface erosion mechanism was unique to the TAF/EVG insert. FIGS. 13 and 14 show the dissolution and disintegration over time for solid dosage forms in simulated vaginal fluid and simulated rectal fluid, respectively.

Surface erosion provided notable benefits over bulk erosion. The bulk erosion process depended on the volume of the dosage form and thus due to degradation, the volume of the dosage form decreased causing the erosion rate to decrease with time. Therefore, bulk erosion rates were difficult to control. On the contrary, solid dosage forms in accordance with the present invention exhibited surface erosion, which is beneficial since the erosion process was constant zero order and was independent of the volume of the dosage form. The surface erosion associated with the present invention was unexpected and provided benefits such as consistent robust dissolution results that were not obtained with bulk erosion dosage form formulations.

The solid dosage form inserts appeared to disintegrate/dissolve through the process of surface erosion as observed visually and shown in the images in SVF (pH 4.3) and PBS (pH 7.2) and dissolved completely in both SVF and PBS solution with no residue observed after the inserts were completely dissolved. Stability was unexpectedly excellent. The mucoadhesive properties of mucin (~0.018 N±0.009) tested with an insert was significantly lower compared to the TAF/EVG inserts with average detachment force with the porcine vaginal tissue (~0.317 N±0.188). There was no change in the dissolution profiles of TAF/EVG inserts when stored at 30° C./65% RH and 40° C./75% RH compared to the initial dissolution profile. The TAF/EVG inserts were found to be stable based on the stability studies data and projected to be stable for a minimum of 2 years when stored at or below 30° C. Overall, these results are a good indicator of the ability of the TAF/EVG inserts to be bioadhesive to the vaginal mucosa for an efficient local drug delivery of TAF (tenofovir alafenamide fumarate) and EVG (elvitegravir) to the vaginal mucosa.

Table 9 provides an exemplary insert formulation in accordance with one aspect of the present invention. The composition exhibited efficacy in non-human primate model.

TABLE 9

Compositions of TAF/EVG, 20 mg/16 mg insert formulation

| Materials | % w/w per Insert | Weight per Insert (500 mg) | Functional Roles | Compendial Grade |
|---|---|---|---|---|
| Tenofovir Alafenamide Fumarate (TAF) salt form* | 4.48 | 22.4* | API | GMP |
| Elvitegravir (EVG) | 3.20 | 16.0 | API | GMP |
| Povidone (K-29/32) | 4.00 | 20.0 | Binder, Disintegrant | USP |
| Poloxamer 188 | 2.00 | 10.0 | Disintegrant | NF, EP, JPE |
| Lactose anhydrous | 52.92 | 264.6 | Diluent | NF |
| Mannitol | 16.90 | 84.5 | Bulking agent | USP |
| PEG 8000 | 15.00 | 75.0 | Lubricant/ Bioadhesive polymer | NF |
| Magnesium Stearate | 1.50 | 7.5 | Lubricant | NF |

*22.4 mg of Tenofovir Alafenamide Fumarate (TAF) salt is equivalent to 20 mg of Tenofovir Alafenamide (TAF) free base.

Demonstration of Antiviral Activity in Humans

The TAF/EVG solid dosage forms disclosed in Table 9 were tested in women in the clinical trial CONRAD 146 (ClinicalTrials.gov number NCT03762772). Women (N=16) self-administered a single insert vaginally and provided vaginal fluid and cervical tissue samples, 4 and 24 hrs post-dose, for anti-HIV and anti-HSV activity evaluation.

Figure 15A:
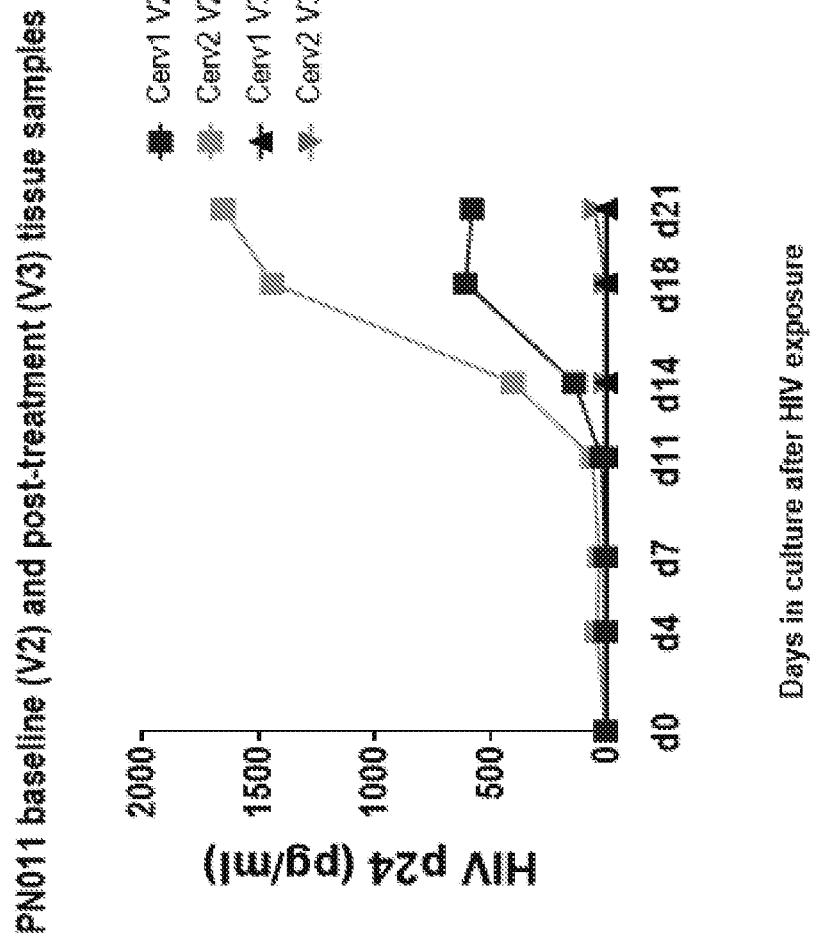
FIG. 15A and FIG. 15B show examples of complete protection against HIV infection ex vivo in baseline and post-treatment cervical tissue samples of two clinical trial participants.
Figure 15B:
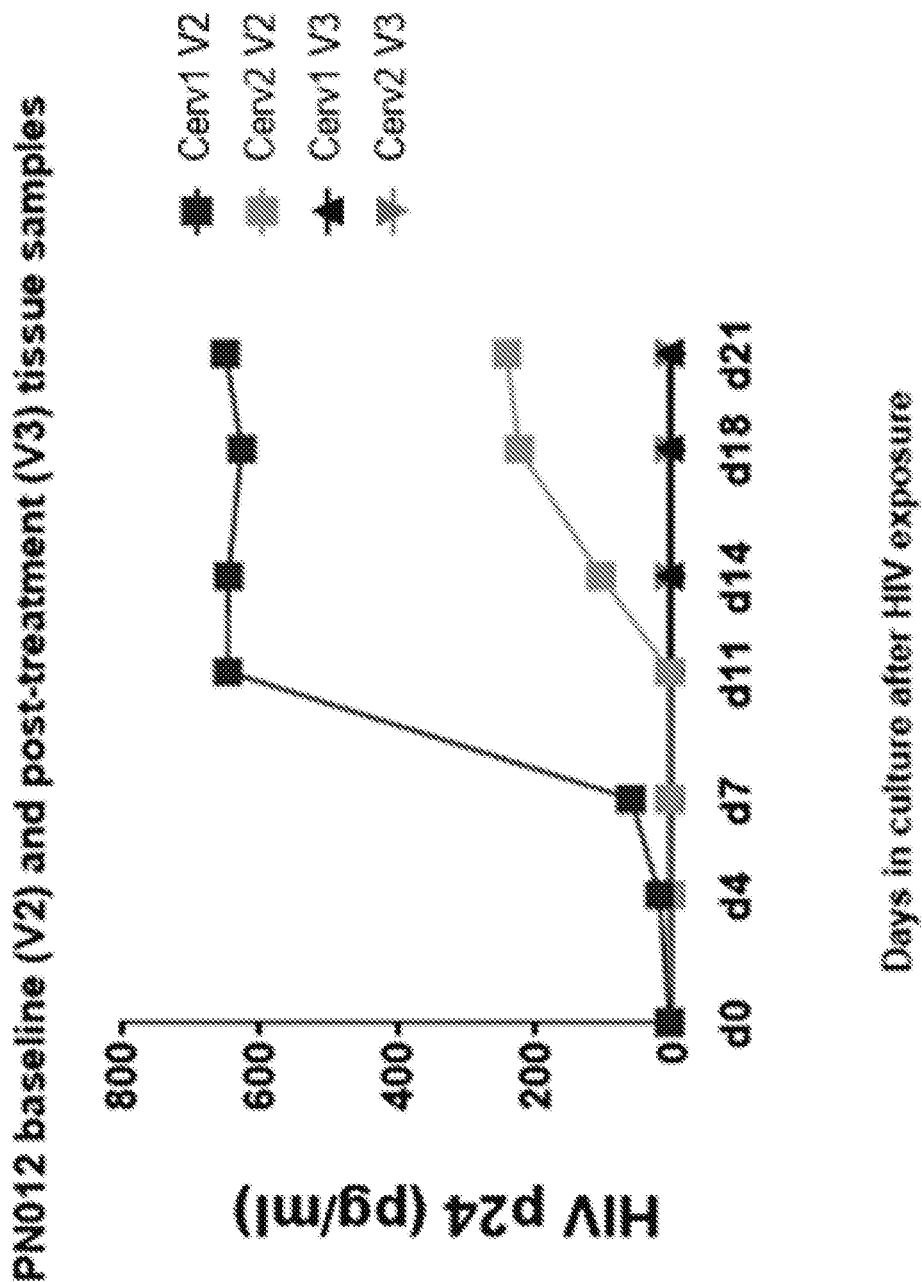

FIG. 15A and FIG. 15B show examples of complete protection against HIV infection ex vivo in baseline and post-treatment cervical tissue samples of two clinical trial participants. This data showed that human genital tissues are protected from HIV infection after topical application of TAF and/or EVG when solid dosage form inserts in accordance with the present application are administered.

Figure 16:
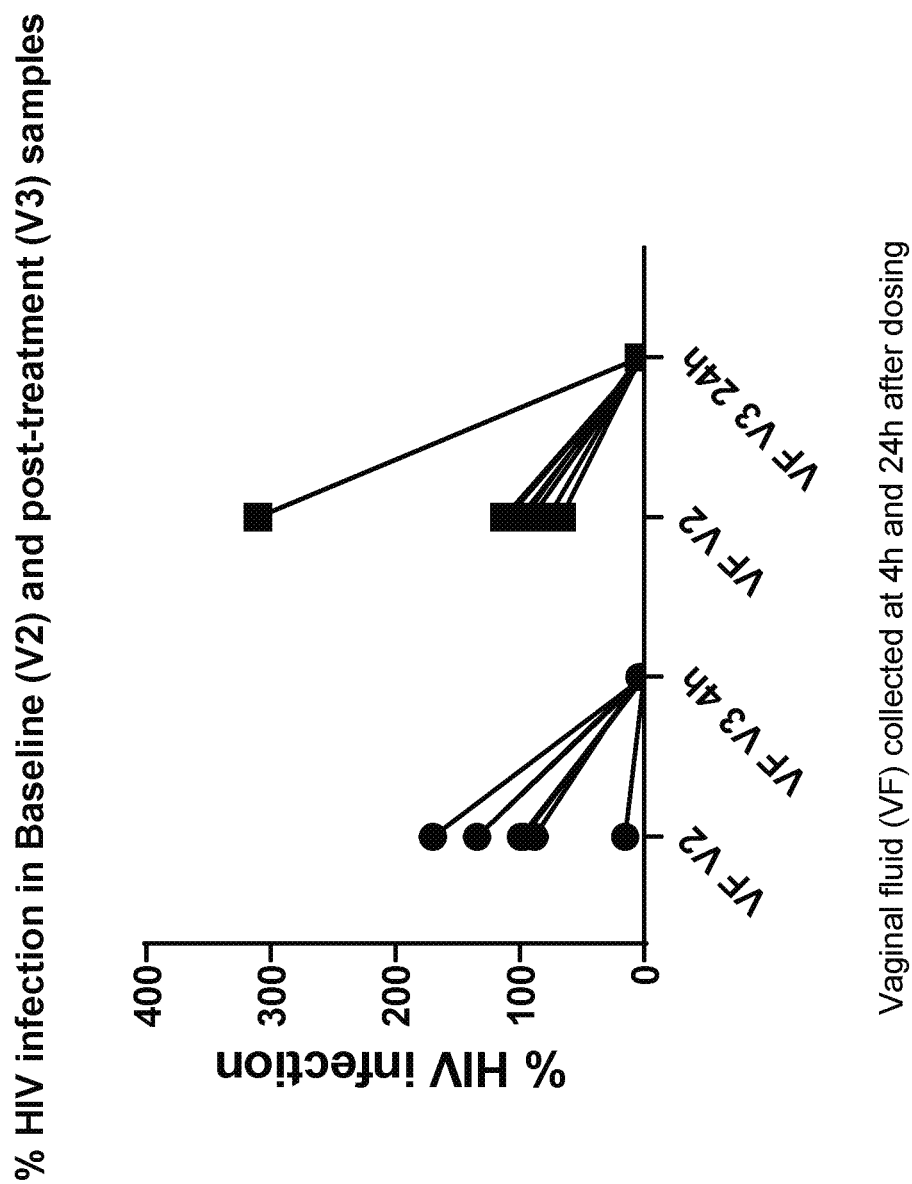
FIG. 16 shows anti-HIV activity of vaginal fluid samples collected 4 and 24 hours after insert application.

FIG. 16 shows anti-HIV activity of vaginal fluid samples collected 4 and 24 hours after insert application. Surprisingly, the inserts inhibited HIV infection even at 24 h after administration, conferring long-lasting protection.

Figure 17:
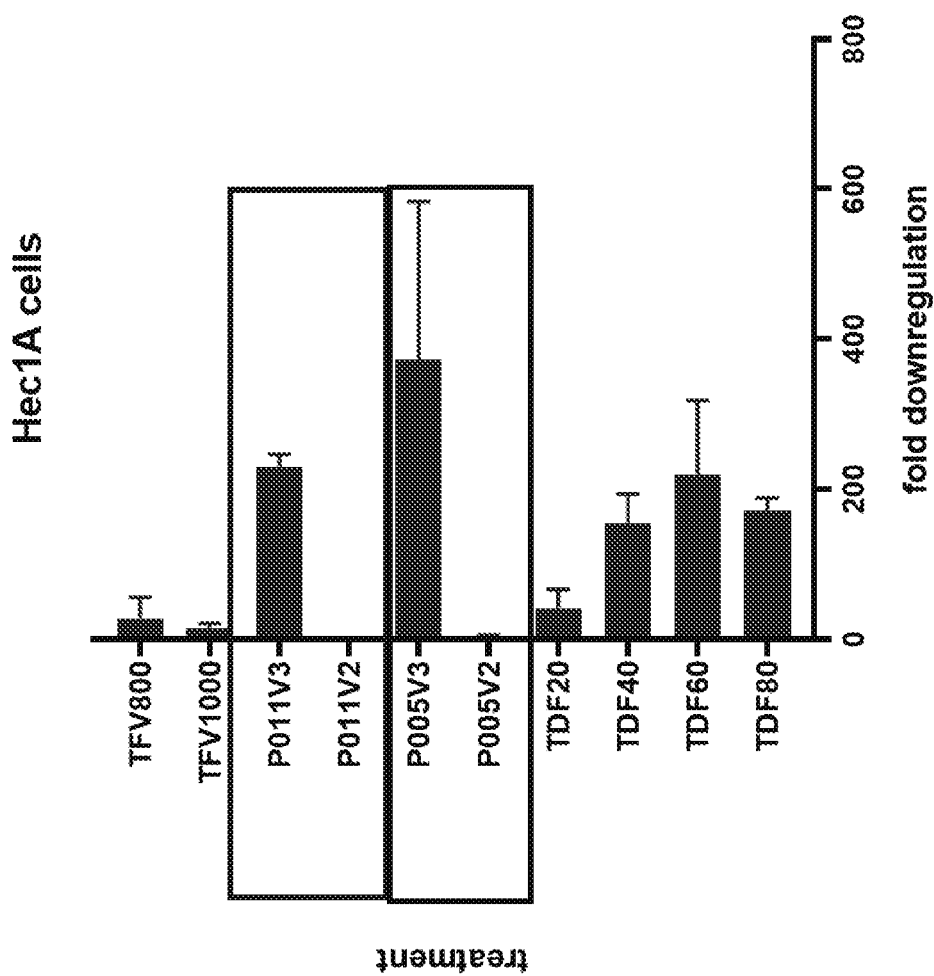
FIG. 17 shows the anti-HSV (herpes) activity of vaginal fluid samples of two clinical trial participants collected at baseline (V2) and post-treatment (V3).

FIG. 17 shows the anti-HSV (herpes) activity of vaginal fluid samples of two clinical trial participants collected at baseline (V2) and post-treatment (V3). Significant decrease (specific gene downregulation) in HSV replication in HEC1A cells was seen in V3 post-treatment samples. This is believed to be the first time that this phenomenon, inhibition of herpes infection of genital tract cells, has been seen with human vaginal fluid samples exposed to TAF/EVG. TFV and TDF represent assay controls.

What is claimed is:

1. A pharmaceutical composition comprising:
   a. a therapeutically effective amount of one or more antiviral active pharmaceutical ingredients; and
   b. one or more pharmaceutically acceptable excipient, wherein said one or more pharmaceutically acceptable excipient comprises:
   a binder in an amount from about 0.5% to about 8% by weight;
   a water-soluble disintegrating agent in an amount from about 0.5% to about 4% by weight; and
   a bioadhesive polymer in an amount from about 5% to about 30% by weight,
   wherein said pharmaceutical composition provides a therapeutically effective amount of the antiviral active pharmaceutical ingredient to vaginal or rectal mucosa when administered topically, wherein the bioadhesive polymer is selected from the group consisting of: PEG 4000, PEG 6000 and PEG 8000.

2. A pharmaceutical composition comprising:
   a. a therapeutically effective amount of one or more antiviral active pharmaceutical ingredients; and
   b. one or more pharmaceutically acceptable excipient, wherein said one or more pharmaceutically acceptable excipient comprises:
   a binder in an amount from about 0.5% to about 8% by weight;
   a water-soluble disintegrating agent in an amount from about 0.5% to about 4% by weight; and
   a bioadhesive polymer in an amount from about 5% to about 30% by weight,
   wherein said pharmaceutical composition provides sustained release of said antiviral active pharmaceutical ingredient when administered as a vaginal or rectal insert, wherein the bioadhesive polymer is selected from the group consisting of: PEG 4000, PEG 6000 and PEG 8000.

3. A solid dosage form comprising:
   a. a therapeutically effective amount of one or more antiviral active pharmaceutical ingredients; and
   b. one or more pharmaceutically acceptable excipient, wherein said one or more pharmaceutically acceptable excipient comprises:
   a binder in an amount from about 0.5% to about 8% by weight;
   a water-soluble disintegrating agent in an amount from about 0.5% to about 4% by weight; and
   a bioadhesive polymer in an amount from about 5% to about 30% by weight,
   wherein said solid dosage form exhibits a mucoadhesive detachment force of at least 0.1 N when measured in accordance with test method described herein with porcine vaginal mucosa, wherein the bioadhesive polymer is selected from the group consisting of: PEG 4000, PEG 6000 and PEG 8000.

4. The solid dosage form of claim 3, wherein the dosage form comprises about 1.5% to about 15% by weight of antiviral active pharmaceutical ingredients.

5. The solid dosage form of claim 3, wherein said one or more active pharmaceutical ingredients comprise an NRTI and an integrase inhibitor.

6. The solid dosage form of claim 3, wherein said one or more active pharmaceutical ingredients comprise tenofovir alafenamide fumarate (TAF) and elvitegravir (EVG).

7. The solid dosage form of claim 6, wherein said tenofovir alafenamide fumarate (TAF) is present in an amount from about 2% to 8% TAF as free base and said elvitegravir (EVG) is present in an amount from about 1.6% to 4.8%.

8. The solid dosage form of claim 3, wherein said one or more pharmaceutically acceptable excipient comprises povidone.

9. The solid dosage form of claim 8, wherein said povidone comprises povidone K29/32, povidone K30 or a mixture thereof.

10. The solid dosage form of claim 3, wherein said one or more pharmaceutically acceptable excipient comprises poloxamer 188 present in an amount from 0.5 to 4% by weight.

11. The solid dosage form of claim 3, wherein said one or more pharmaceutically acceptable excipient comprises lactose present in an amount from about 25% to 75% by weight.

12. The solid dosage form of claim 3, wherein said one or more pharmaceutically acceptable excipient comprises a sugar alcohol present in an amount from about 5% to 30% by weight.

13. The solid dosage form of claim 12 wherein said sugar alcohol is selected from the group consisting of mannitol, glycerol, erythritol, xylitol, sorbitol, isomalt, maltitol, lactitol, and mixtures thereof.

14. The solid dosage form of claim 3, wherein said one or more pharmaceutically acceptable excipient comprises PEG present in an amount from about 5 to 30% by weight.

15. The solid dosage form of claim 3, wherein said one or more pharmaceutically acceptable excipient comprises a lubricant selected from the group consisting of magnesium stearate, stearic acid, sodium stearyl fumarate, glycerol monostearate, colloidal silicon dioxide, talc, calcium stearate and mixtures thereof in the concentration ranging from 0.2-4% by weight.

16. The solid dosage form of claim 3, wherein said one or more pharmaceutically acceptable excipient comprises a hydrophilic excipient.

17. The solid dosage form of claim 3 wherein:
said one or more active pharmaceutical ingredients comprises TAF and EVG;
said binder comprises povidone;
said water soluble disintegrating agent comprises poloxamer 188; and
said bioadhesive polymer comprises PEG 8000.

18. The solid dosage form of claim 3, wherein the dosage form further comprises an antibiotic.

19. The solid dosage form of claim 18, wherein the antibiotic is selected from the group consisting of tetracyclines, macrolides, lincosamides, nitroimidazoles and mixtures thereof.

20. The solid dosage form of claim 18, wherein the antibiotic is selected from the group consisting of doxycycline, doxycycline hyclate, doxycycline anhydrous, doxycycline monohydrate, azithromycin, clindamycin, metronidazole, tinidazole, secnidazole and mixtures thereof.

21. A method for treating or preventing a viral infection in a subject comprising administering the solid dosage form in accordance with claim 3 to the subject.

22. The method of claim 21 wherein the viral infection is selected from the group consisting of HIV, HSV and HBV.

23. The method of claim 21 further comprising treating another infection.

24. The method of claim 23 wherein the another infection is selected from the group consisting of chlamydia, gonorrhea, bacterial vaginosis, trichomoniasis and syphilis.

25. The method of claim 23 wherein the viral infection is selected from the group consisting of HIV, HSV and HBV.

* * * * *